United States Patent [19]
Santilli et al.

[11] Patent Number: 6,015,930
[45] Date of Patent: Jan. 18, 2000

[54] METHOD OF MAKING 2,6-DIMETHYLNAPHTHALENE FROM OTHER DIMETHYLNAPHTHALENE ISOMERS AND FROM DIMETHYLTETRALINS/DIMETHYLDECALINS WITH A METHYL GROUP ON EACH RING

[75] Inventors: Donald S. Santilli, Larkspur; Cong-Yan Chen, Richmond, both of Calif.

[73] Assignee: Chevron Chemical Company, San Ramon, Calif.

[21] Appl. No.: 08/892,508

[22] Filed: Jul. 14, 1997

[51] Int. Cl.[7] .................................. C07C 1/00; C07C 5/22
[52] U.S. Cl. ........................... 585/320; 585/321; 585/480; 585/481; 585/482
[58] Field of Search ..................... 585/320, 321, 585/480, 481, 482

[56] References Cited

U.S. PATENT DOCUMENTS

| | | | |
|---|---|---|---|
| 3,890,403 | 6/1975 | Shimada et al. | 585/320 |
| 5,004,853 | 4/1991 | Barger et al. | 585/482 |

*Primary Examiner*—Walter D. Griffin
*Assistant Examiner*—In Suk Bullock
*Attorney, Agent, or Firm*—W. Bradley Haymond

[57] ABSTRACT

The invention discloses a method of making 2,6-dimethylnaphthalene from any DMN with one methyl on each ring in a two-step hydroisomerization/dehydrogenation process. The catalyst used in the hydroisomerization step is an acidic catalyst such as a silica aluminum catalyst with a hydrogenation/dehydrogenation metal. The catalyst used in the dehydrogenation step is a reforming type catalyst.

18 Claims, 27 Drawing Sheets

METHOD OF MAKING 2,6-DIMETHYLNAPHTHALENE FROM OTHER DIMETHYLNAPHTHALENE ISOMERS AND FROM DIMETHYLTETRALINS/DIMETHYLDECALINS WITH A METHYL GROUP ON EACH RING

FIELD OF THE INVENTION

The present invention relates to a method for making 2,6-dimethylnaphthalene from a hydrocarbon feed comprising isomers of dimethylnaphthalene (DMN) and dimethyltetralins/dimethyldecalins (DMT/DMD) having a methyl group on each ring.

BACKGROUND OF THE INVENTION

There are ten different isomers of dimethyinaphthalene (DMN). Of these, nine of them can be grouped into three triads based on the relative ease of isomerization within a certain triad. Such an intra-triad isomerization can be done using a wide variety of solid acids as catalysts. This ease of isomerization within a triad is based on the fact that a methyl group on naphthalene shifts relatively easily from an alpha position to a beta position or vice versa on the same ring but does not shift easily from a beta position to another beta position on the same ring or from an alpha position to another alpha position. The three triad groups are as follows: 2,7-, 1,7- and 1,8-dimethylnaphthalene; 2,6-, 1,6- and 1,5-dimethylnaphthalene; and 1,4-, 1,3- and 2,3-dimethylnaphthalene. 1,2-dimethylnaphthalene is the tenth isomer and doesn't fit into any of the three triads. Although isomerization of dimethylnaphthalenes within these triad groups is relatively easy, isomerization from one triad group to another triad group is much more difficult. Since certain of the isomers of dimethylnaphthalene are much more valuable than others for use in plastics synthesis, investigators are continually making attempts to find ways of converting from less useful to more useful isomers. A particularly valuable isomer is 2,6-dimethylnaphthalene. Certain processes for synthesizing dimethylnaphthalenes result in high yields of 2,7- and 1,7-dimethylnaphthalenes. Conversion of 2,7- and 1,7-dimethylnaphthalenes into 2,6-dimethylnaphthalene has been accomplished using certain zeolites such as ZSM-5. However, such conversion has resulted in an excess of undesirable side products such as methylnaphthalenes, trimethylnaphthalenes and 1,4-, 1,3- and 2,3-dimethylnaphthalene via dealkylation, cracking and transalkylation. Usually, this acid-catalyzed isomerization is associated with catalyst deactivation as the reaction goes on, resulting in a short catalyst life.

It would be very useful to find an economical way to convert 2,7- and 1,7-dimethylnaphthalene which occur as abundant products in dimethylnaphthalene synthesis to 2,6-dimethylnaphthalene in a high yield.

Other investigators have found methods of converting the dimethylnaphthalene isomers, particularly 2,7-dimethynaphthalene to the most useful, and therefore most valuable isomer, 2,6-dimethylnaphthalene, but none of these conversion methods have been sufficiently simple and economical to warrant the general use of such methods.

U.S. Pat. No. 3,890,403 (Shimada et al.) discloses a method which can reportedly be used to obtain 2,6-dimethylnaphthalene from a dimethylnaphthalene mixture containing the various isomers of dimethylnaphthalene. The method involves (a) partially hydrogenating the dimethylnaphthalene mixture to obtain dimethyltetralins (DMT) with a hydrogenation catalyst such as nickel, platinum, palladium, rhodium, copper-chromium, iridium or ruthenium; (b) isomerizing the dimethyltetralins with a solid acid catalyst such as a zeolite catalyst so that the dimethyltetralin isomers in which the two methyl groups occur on the same ring can be converted to the dimethyltetralin isomers in which the two methyl groups occur on opposite rings and the amount of dimethyltetralin isomers in which the two methyl groups occur on opposite rings is brought near to thermodynamical equilibrium; (c) separating and collecting the dimethyltetralin isomers in which the two methyl group occur on opposite rings from the isomers in which the two methyl groups occur on the same ring; (d) dehydrogenating the collected DMT mixture to convert it into a DMN mixture; (e) separating and recovering 2,6-DMN from the recovered DMN mixture. Although this method obtains the desirable 2,6-DMN isomer from other DMN isomers, the method is quite time-consuming and expensive because it involves several quite separate and distinct steps.

U.S. Pat. No. 3,803,253 (Suld) discloses a process of hydroisomerization/dehydrogenation of a mixture of dimethylnaphthalenes, so that 2,6-dimethylnaphthalene can be obtained and isolated out from the reaction mixture. The other remaining products are then recycled and the process is repeated to obtain more 2,6-dimethylnaphthalene. The catalyst used for the hydroisomerization/dehydrogenation step is described as a combination of a calcium-containing faujasite and a hydrogenation/dehydrogenation catalyst component. The process step, with hydroisomerization and dehydrogenation performed simultaneously in the same reaction vessel in the presence of the described combination catalyst, simplifies the process but makes the overall efficiency and yield of the process quite low.

U.S. Pat. No. 3,928,482 (Hedge et al.), which is related to '253 discussed above, discloses a hydroisomerization process by which 2,6-DMT is obtained from a feed mixture which is rich in 2,7- or 1,7-DMT using an aluminosilicate zeolite containing polyvalent metal cations in exchange positions. This process is intended to be incorporated as an improvement to the method of '253 discussed above but does not overcome the basic lack of success of that process for obtaining 2,6-DMN in high yields in a cost-effective way.

An economical method of obtaining 2,6-DMN from other DMN isomers, especially isomers in the 2,7-DMN triad, with few steps and at relatively high yields is needed. The present inventors have found such a method.

SUMMARY OF THE INVENTION

One object of the present invention is to provide an economical method of making 2,6-dimethylnaphthalene in relatively high and stable yields.

Another object of the present invention is to provide a method of utilizing a dimethylnaphthalene isomer or mixture of isomers selected from the group consisting of 1,6-dimethylnaphthalene, 1,5-dimethylnaphthalene, 2,7-dimethylnaphthalene, 1,7-dimethylnaphthalene, 1,8-dimethylnaphthalene and partially or fully hydrogenated counterparts thereof to produce 2,6-dimethylnaphthalene.

Still another object of the present invention is to provide a method of making 2,6-dimethylnaphthalene with no significant formation of naphthalene, methylnaphthalenes, trimethylnaphthalenes and 1,4-, 1,3-, 2,3- and 1,2-dimethylnaphthalene.

Yet another object of the present invention is to provide a method of making 2,6-dimethylnaphthalene using a two-step hydroisomerization/dehydrogenation process.

An additional object of the present invention is to provide a method of making 2,6-dimethylnaphthalene using a two-step hydroisomerization/dehydrogenation process in conjunction with an intra-triad isomerization process in which 1,7- and 1,8-DMN are converted on an acid catalyst to 2,7-DMN and 1,6- and 1,5-DMN are converted on an acid catalyst to 2,6-DMN, respectively, the 2,6-DMN is separated out and the 2,7-DMN is then converted to 2,6-DMN with the hydroisomerization/dehydrogenation process.

Another object of the present invention is to provide a method of utilizing an acid catalyst in a hydroisomerization step followed by a reforming or dehydrogenation catalyst in a dehydrogenation step to convert 2,7-dimethylnaphthalene triad isomers (especially 2,7- and 1,7-DMN) to 2,6-dimethylnaphthalene triad isomers (especially 2,6- and 1,6-DMN).

Other features and advantages of the invention will be apparent from the following description.

DETAILED DESCRIPTION OF THE INVENTION

Figure 1A:
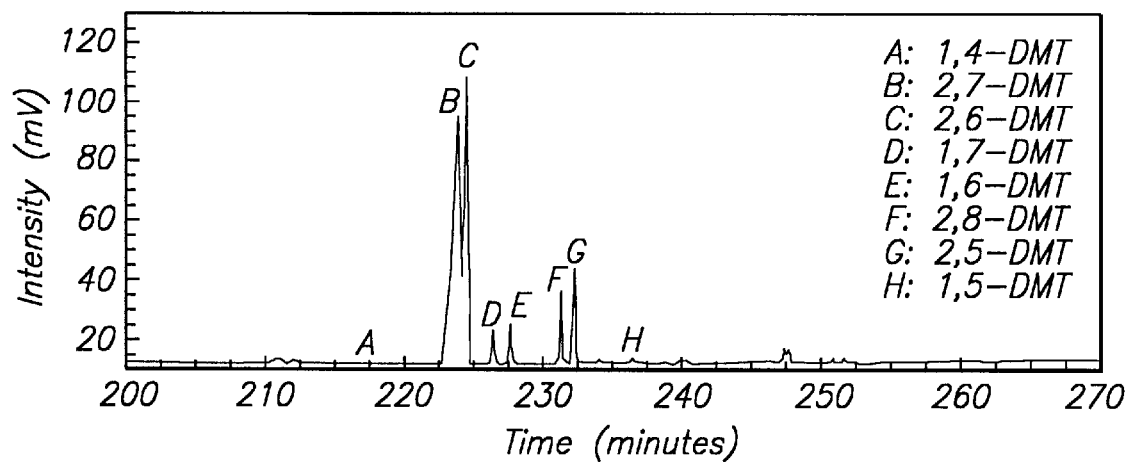
FIG. 1a shows in an expanded chromatographic form the DMT isomers which are the product of the hydroisomerization run described in Example 8 and shown in a larger scale in FIG. 10b.

This invention relates to a method of making 2,6-dimethylnaphthalene. Specifically, the invention relates to a method of using dimethylnaphthalene isomer or mixture of isomers selected from the group consisting of 1,6-dimethylnaphthalene, 1,5-dimethylnaphthalene, 2,7-dimethylnaphthalene, 1,7-dimethylnaphthalene, 1,8-dimethylnaphthalene, and partially or fully hydrogenated counterparts thereof to obtain 2,6-dimethylnaphthalene. The invention also relates to using an acid catalyst (the catalyst's acidity being measured by the catalyst's positive adsorption of ammonia, pyridine, and piperidine probes on its surface sites) with a metal in a hydroisomerization step followed by a reforming catalyst in a dehydrogenation step to obtain 2,6-dimethylnaphthalene from a dimethylnaphthalene isomer or mixture of isomers selected from the group consisting of 1,6-dimethylnaphthalene, 1,5-dimethylnaphthalene, 2,7-dimethylnaphthalene, 1,7-dimethylnaphthalene, 1,8-dimethylnaphthalene, and partially or fully hydrogenated counterparts thereof. The invention further relates to the use of a metal with an acid catalyst. This can be any metal that is effective as a catalyst in hydrogenation reactions, such as, for example, palladium, nickel, copper or platinum. In another preferred embodiment, the acid catalyst is used with a metal in a range of from 0.1 to 30 weight %. In one preferred embodiment, the metal used with the acid catalyst is palladium. In another preferred embodiment, the metal used with the acid catalyst is platinum. In yet another preferred embodiment, the metal is sulfided. Non-limiting examples of hydroisomerization catalysts which can be used are PdS/Boron-Beta (in the presence of 500 ppm aluminum), PtS/Boron-Beta (in the presence of 500 ppm aluminum), PdS/Y, and non-sulfided Pd/Boron-Beta (in the presence of 500 ppm aluminum). PtS/Boron-SSZ-33 is not as effective as a hydroisomerization catalyst because of its tendency to serve only a hydrogenating function and not to isomerize the various DMN isomers to the 2,6-DMD or -DMT isomer.

A possible mechanism for the process of obtaining 2,6-dimethylnaphthalene from 2,7-, 1,7-, 1,8-, 1,5- and 1,6-dimethylnaphthalene with the acid catalyst and the noble metal could relate to dimethylnaphthalenes being partially or fully saturated to dimethyltetralins or dimethyldecalins on or in the catalyst. According to this possible mechanism, once at least one of the aromatic rings in dimethylnaphthalenes is saturated, the beta-beta migration of methyl groups becomes much easier because the energy barriers for such a migration are lifted by changing the reaction pathways. It appears, according to this mechanism, that if there is sufficient acidity on or in the catalyst, the saturated DMN's will isomerize near to equilibrium.

After the above hydroisomerization, the saturated dimethylnaphthalenes must be reformed back to unsaturated dimethylnaphthalenes by dehydrogenation. For this step to work with high selectivity, i.e., avoiding non-2,6-dimethylnaphthalenes, the reforming step should be done over a catalyst which avoids transalkylation, dealkylation, and cracking reactions. In a preferred embodiment, catalysts that can be used in the reforming step are both acidic and non-acidic catalysts. A non-limiting example of an acidic catalyst that can be used is a mixture of rhenium and platinum on alumina (sulfided Pt/Re/Al$_2$O$_3$). Non-limiting examples of a non-acidic catalyst that can be used are sulfided Pt/Na-ZSM-5 and PtS/Cs/Boron-SSZ42.

An alternative method of obtaining 2,6-DMN from other DMN isomers, particularly those in the 2,7-DMN triad, is by means of an acid-catalyzed DMN isomerization. Unlike the hydroisomerization/dehydrogenation two-step process discussed above, this process proceeds in one step and does not involve the partially or fully saturated intermediate DMT and/or DMD forms. A non-limiting example of a catalyst that can be used for such an acid-catalyzed isomerization is H-ZSM-11. This process is less preferred than the hydroisomerization/dehydrogenation process discussed above because it has a tendency to produce a fair amount of methylnaphthalenes (MN) and trimethyinaphthalenes (TMN) as well as the undesired isomers of DMN. Thus, its yield of 2,6-DMN is low in comparison to the hydroisomerization/dehydrogenation process.

In all the embodiments of the hydroisomerization/dehydrogenation process, the dimethylnaphthalene feed (neat or in solution) can be flowed over the catalyst along with hydrogen gas or the reaction can be performed batchwise. In this process, the temperature needs to be high enough to hydrogenate the dimethylnaphthalene feed and to isomerize the resulting DMD's and DMT's. The hydroisomerization reaction depends on both the hydrogenation/dehydrogenation activity and acid strength of the catalyst. Additionally, in order to generate a significant amount of DMT/DMD's, the hydrogen pressure needs to be sufficiently high. Thermodynamically, higher temperatures drive the equilibrium towards DMN while higher hydrogen pressures help shift the equilibrium towards the saturated species (DMD). The reaction kinetics, which are dependent on the catalyst type, also have a strong influence on the product selectivity in relation to the hydrogenation/dehydrogenation activity and acid strength of the catalyst. In a preferred embodiment, the yield of partially saturated species (DMT) from the hydroisomerization reaction should be at least 5 weight percent. In a more preferred embodiment, the yield of partially saturated species (DMT) should be at least 10 weight percent. Accordingly, the Weight Hourly Space Velocity (WHSV) can be varied over a broad range (e.g., about 0.1 to 100 $h^{-1}$), the pressure can vary from 0 to 3000 psig, the hydrogen/hydrocarbon molar ratio can vary from ~0.0 to 100, and the reactor temperature can vary from about 300 to 1000° F. The unreacted material and the partially hydrogenated products other than 2,6-isomers can be recycled back to the reactor or reformed back to DMN's in a separate reactor. Various product separation schemes can be used at different points of the process. Also, in one embodiment, a more conventional isomerization process to interconvert isomers within triads can be used in conjunction with this process.

In both the hydroisomerization and the reforming step, there are many variables to be optimized. These include: run temperature, pressure, space velocity, and the catalyst itself. As shown below, when such variables are optimized, approximately 50% conversion of 2,7- to 2,6-triad can be achieved. The resulting non-2,6-DMN $C_{12}$-isomers can be separated from 2,6-DMN product and recycled to the hydroisomerization reactor to be further converted to 2,6-DMN, boosting the 2,6-DMN production. Furthermore, little or no formation of 1,2-DMN, 1,3-DMN, 1,4-DMN, 2,3-DMN or TMN is encountered. There is also relatively little formation of MN's with the isomerization catalysts used. By taking measures to minimize hydrogenolysis during the isomerization reaction, such as by adding a little sulfur to the feed, formation of MN's can be minimized even further. With such results achieved with the present invention, it is now possible to achieve large scale isomerization of 2,7-, 1,7-, 1,8-, 1,5- and 1,6-DMN to 2,6-DMN. In addition, the yield of 2,6-DMN can be also increased through enhancing the DMN feedstocks by incorporating the more conventional, acid-catalyzed intra-triad isomerization of DMN's into the hydroisomerization/dehydrogenation process. Such intra-triad isomerization of DMN's may be further associated with a recycling step described above.

In experiments described below, various hydroisomerization catalysts were used. In these experiments, there was little evidence of deactivation of the catalysts, in some cases after up to approximately three weeks of continuous use. It was also found in these experiments that the reforming step converted almost all of the saturated species back to DMN's. In fact, a ratio of ~95/5 DMN/saturated species or better can be achieved if the various conditions are optimized.

EXAMPLES

The present invention will be further described with the following tables and figures showing the results of several experiments.

Hydrogenation Without Isomerization

The results of Examples 1–4 with PtS/Boron-SSZ-33 reveal that effective hydroisomerization of DMN's to DMT's requires not only a sufficient hydrogenation/dehydrogenation function such as that of PtS but also a sufficient acidity since PtS/Boron-SSZ-33 tends to serve only a hydrogenating function and not to isomerize the resulting DMT's to other DMT isomers.

Figure 1B:
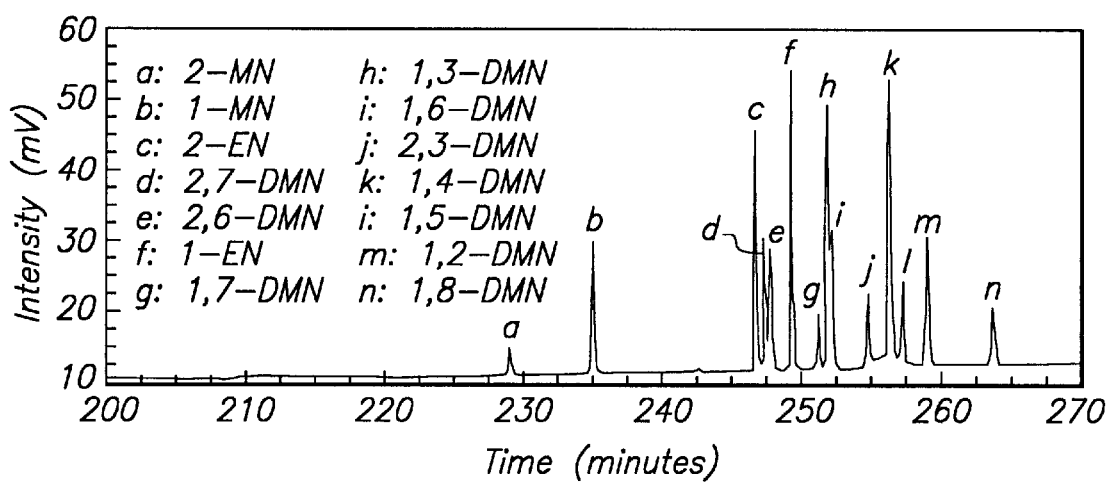
FIG. 1b shows in chromatographic form the DMN, MN and EN isomers, which were measured using GC standards to identify the DMN products to be discussed in the next examples.
Figure 10A:
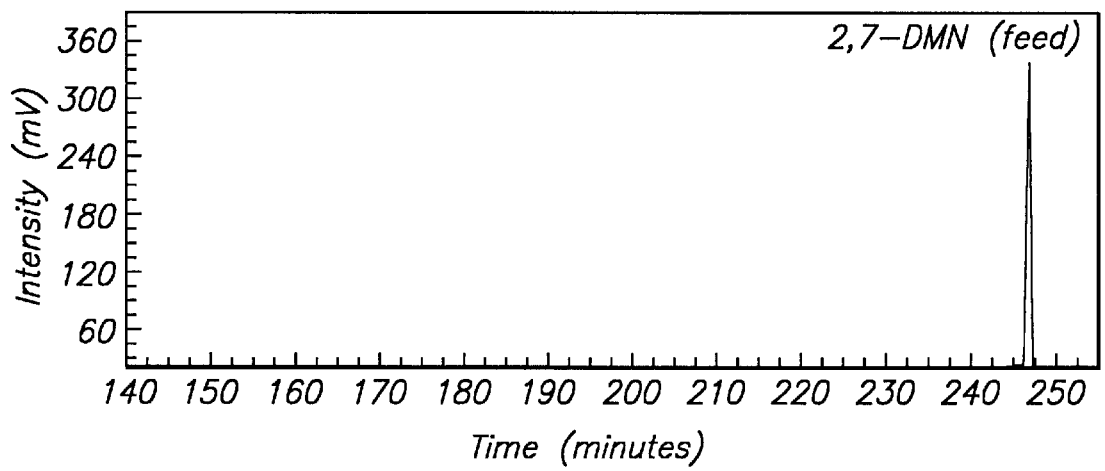
FIG. 10a shows the composition in chromatographic form of the 2,7-DMN feed of the hydroisomerization reaction described in Example 8.
Figure 10B:
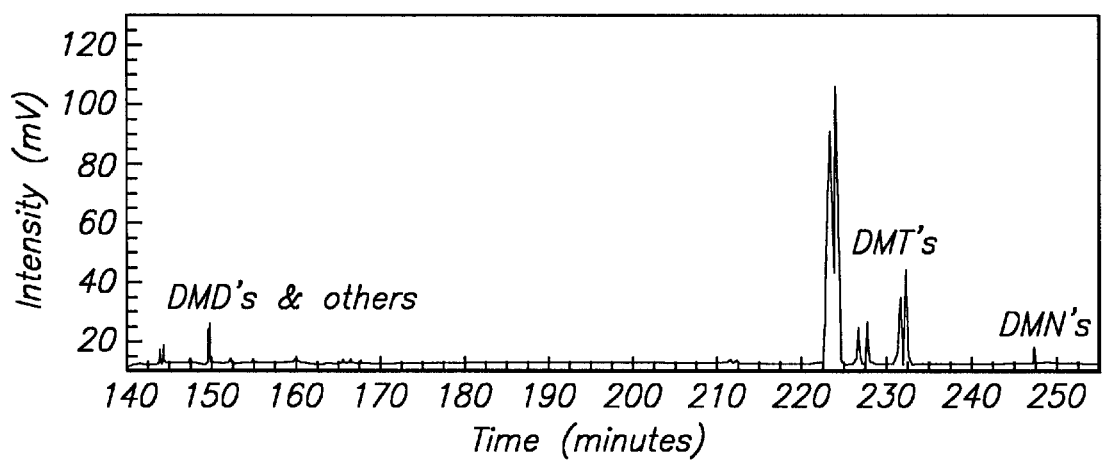
FIG. 10b shows the composition in chromatographic form of the resulting product of the reaction.

Taking advantage of these results, the DMT isomers (1,5-, 1,6-, 2,5-, 1,7-, 2,8- and 2,7-DMT) produced in Examples 1–4, together with 1,4- and 2,6-DMT which are supplied as standards by Chemsampco and API/Carnegie Mellon University, respectively, are used to identify and quantify the major DMT isomers produced in the hydroisomerization step of this invention, as demonstrated in FIG. 1a which is a part of FIG. 10b (see Example 8) on an expanded scale. It is beneficial to have the major DMD's and DMT's, especially DMT's, identified in the hydroisomerization step since it roughly gives the information on how much 2,6-isomers can be produced, useful for the prediction of 2,6-DMN yield even prior to the reforming step to be conducted after the hydroisomerization. Additionally, FIG. 1b shows the methylnaphthalenes (MN), dimethylnaphthalenes (DMN) and ethylnaphthalenes (EN) in chromatographic form, which was measured using GC standards to identify the DMN products to be discussed in the next examples.

Example 1

Hydrogenation of 1,5-DMN with PtS/B-SSZ-33

Figure 2A:
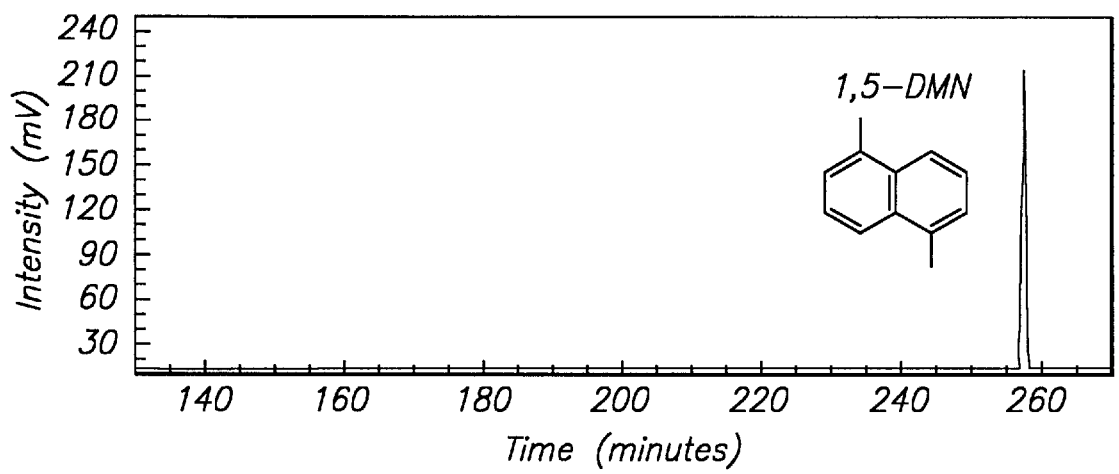
FIG. 2a shows the composition in chromatographic form of the 1,5-DMN feed of the hydrogenation reaction described in Example 1.
Figure 2B:
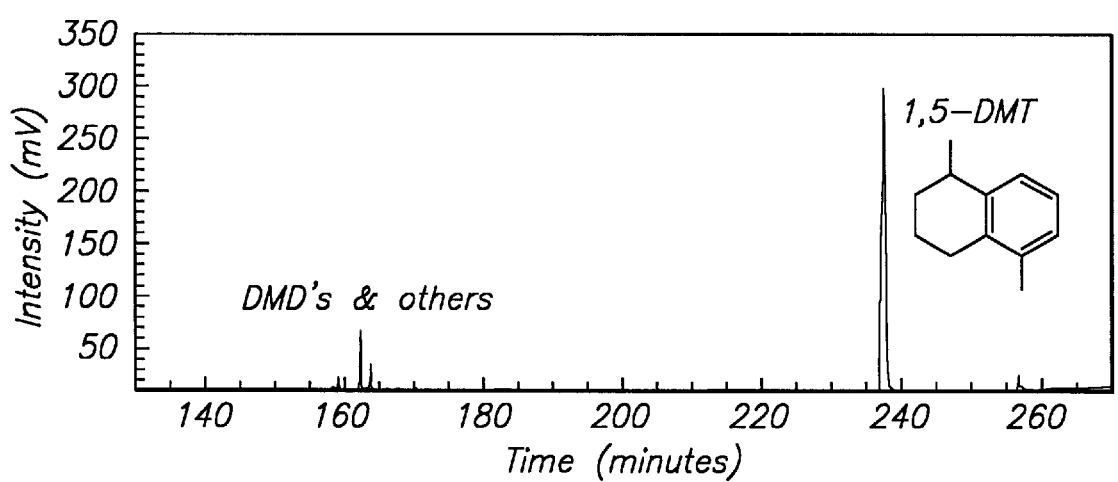
FIG. 2b shows the composition in chromatographic form of the 1,5-DMT product of the reaction.

An experiment was performed to hydrogenate a hydrocarbon feed of 5:1 (wt:wt) o-xylene: 1,5-dimethylnaphthalene in a reactor with a PtS/Boron-SSZ-33 catalyst (0.5 g). The reaction was conducted at 400° F., 200 psig, 1 ml/hr feed and 40 ml/min $H_2$. The result of the experiment is shown in chromatographic form in FIG. 2a (a chromatographic view of the 1,5-DMN feed before the reaction) and FIG. 2b (a chromatographic view of the resulting 1,5-DMT after the reaction). 96% of 1,5-DMN was converted, yielding 88% 1,5-DMT and 8% DMD's and other C12's. No other DMT isomers are observed. The identification of the GC peaks was confirmed by GC/MS analysis. In this example and the examples which follow, the diluent o-xylene and its reaction products are subtracted out of the yield data shown in the tables.

Example 2

Hydrogenation of 1,6-DMN with PtS/B-SSZ-33

Figure 3A:
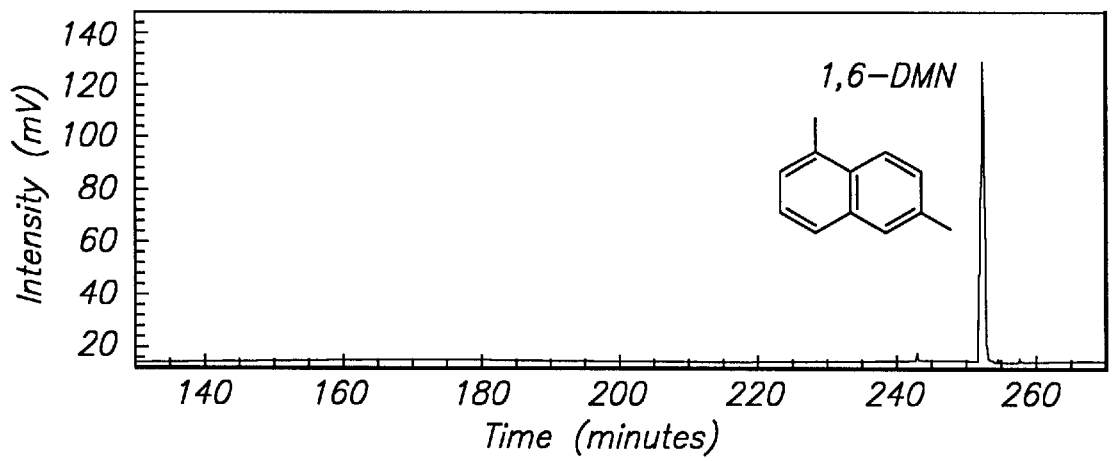
FIG. 3a shows the composition in chromatographic form of the 1,6-DMN feed of the hydrogenation reaction described in Example 2.
Figure 3B:
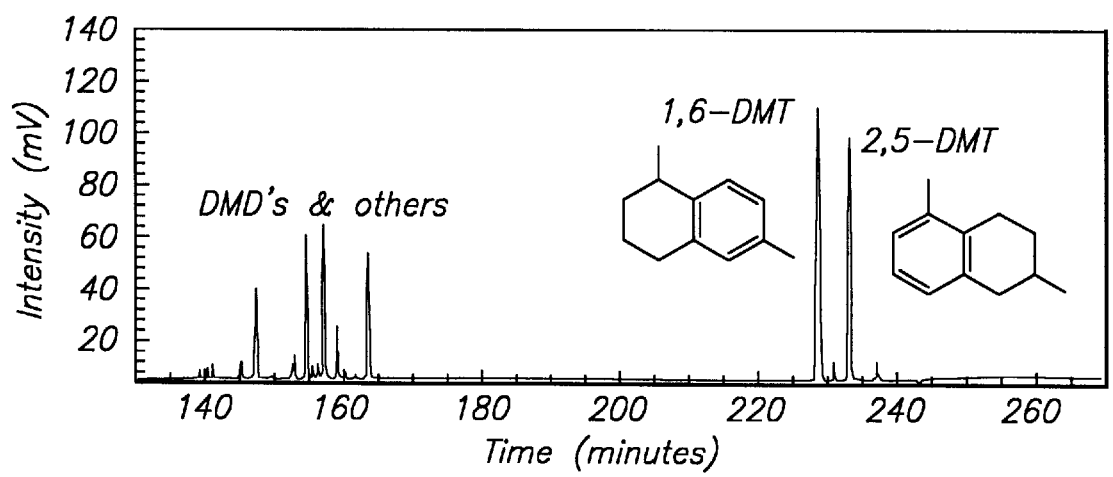
FIG. 3b shows the composition in chromatographic form of the DMT isomers that are the product of the reaction.

An experiment was performed to hydrogenate a hydrocarbon feed of 5:1 (wt:wt) o-xylene: 1,6-dimethylnaphthalene in a reactor with a PtS/Boron-SSZ-33 catalyst (0.5 g). The reaction was conducted at 420° F., 200 psig, 0.5 ml/hr feed and 40 ml/min $H_2$. The result of the experiment is shown in chromatographic form in FIG. 3a (a chromatographic view of the 1,6-DMN feed before the reaction) and FIG. 3b (a chromatographic view of the resulting DMT isomers after the reaction). Depending on which aromatic ring of 1,6-DMN is hydrogenated, two different DMT isomers were produced, namely, 1,6-DMT and 2,5-DMT. Basically, no other DMT's were present in the product. At 100% conversion of 1,6-DMN, 31% 1,6-DMT and 23% 2,5-DMT were yielded with other 46% as DMD's and other C12 species. The identification of the GC peaks was confirmed by GC/MS analysis.

Example 3

Hydrogenation of 1,7-DMN with Pts/B-SSZ-33

Figure 4A:
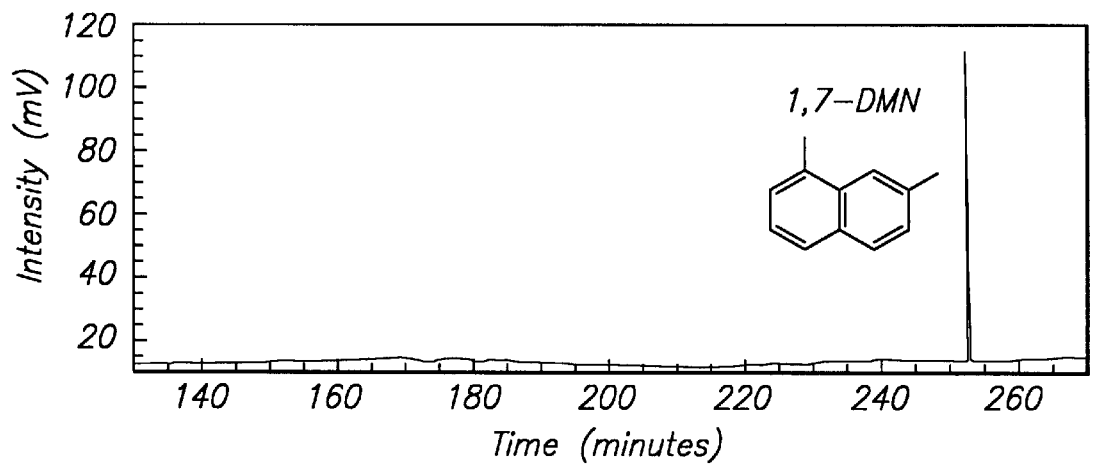
FIG. 4a shows the composition in chromatographic form of the 1,7-DMN feed of the hydrogenation reaction described in Example 3.
Figure 4B:
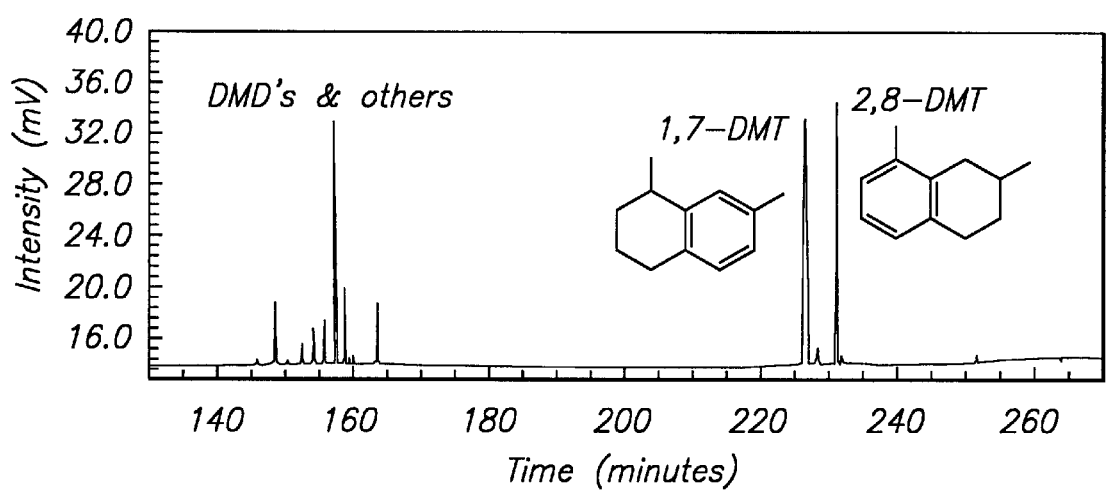
FIG. 4b shows the composition in chromatographic form of the DMT isomers that are the product of the reaction.

An experiment was performed to hydrogenate a hydrocarbon feed of 5:1 (wt:wt) o-xylene: 1,7- dimethylnaphthalene in a reactor with a PtS/Boron-SSZ-33 catalyst (0.5 g). The reaction was conducted at 420° F., 200 psig, 0.5 ml/hr feed and 40 ml/min $H_2$. The result of the run is shown in chromatographic form in FIG. 4a (a chromatographic view of the 1,7-DMN feed before the reaction) and FIG. 4b (a chromatographic view of the resulting DMT isomers after the reaction). Depending on which aromatic ring of 1,7-DMN is hydrogenated, two different DMT isomers were produced, namely, 1,7-DMT and 2,8-DMT. Basically, no other DMT's were present in the product. At ~100% conversion of 1,7-DMN, 26% 1,7-DMT and 28% 2,8-DMT were yielded with the other 46% as DMD's and other C12 species. The identification of the GC peaks was confirmed by GC/MS analysis.

Example 4

Hydrogenation of 2,7-DMN with PtS/B-SSZ-33

Figure 5A:
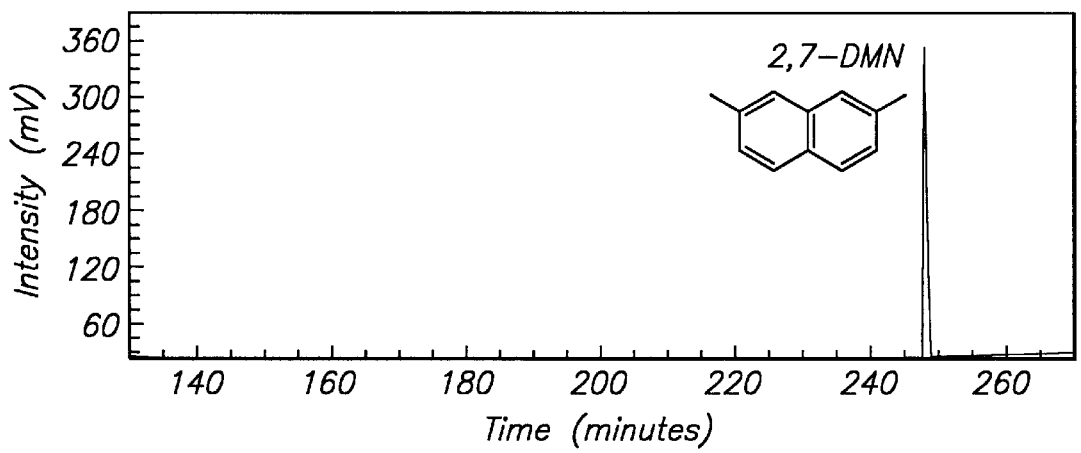
FIG. 5a shows the composition in chromatographic form of the 2,7-DMN feed of the hydrogenation reaction described in Example 4.
Figure 5B:
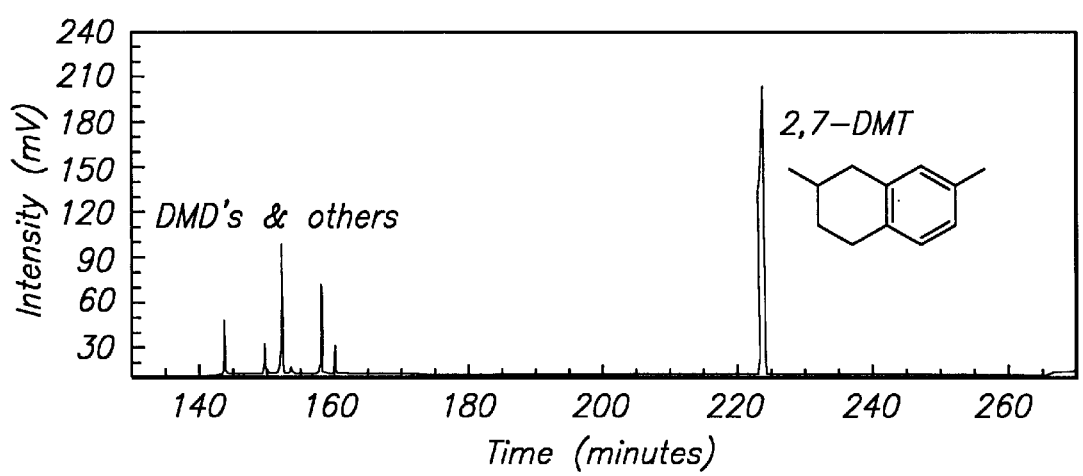
FIG. 5b shows the composition in chromatographic form of the 2,7-DMT resulting from the reaction.

An experiment was performed to hydrogenate a hydrocarbon feed of 5:1 (wt:wt) o-xylene: 2,7-dimethylnaphthalene in a reactor with a PtS/Boron-SSZ-33 catalyst (0.5 g). The reaction was conducted at 380° F., 200 psig, 1 ml/hr feed, and 40 ml/min $H_2$. The result of the experiment is shown in chromatographic form in FIG. 5a (a chromatographic view of the 2,7-DMN feed before the reaction) and FIG. 5b (a chromatographic view of the resulting 2,7-DMT after the reaction). At 100% conversion of 2,7-DMN, 2,7-DMT yield was 75%. Other 25% are DMD's and other C12's. No other DMT isomers are observed. The identification of the GC peaks is confirmed by GC/MS analysis.

Hydroisomerization Without Dehydrogenation

Examples 5–10 describe the results of experiments performing the hydroisomerization step without a subsequent dehydrogenation of the hydroisomerization products.

Example 5

Hydroisomerization of 2,7-DMN with PdS/Y

Figure 6A:
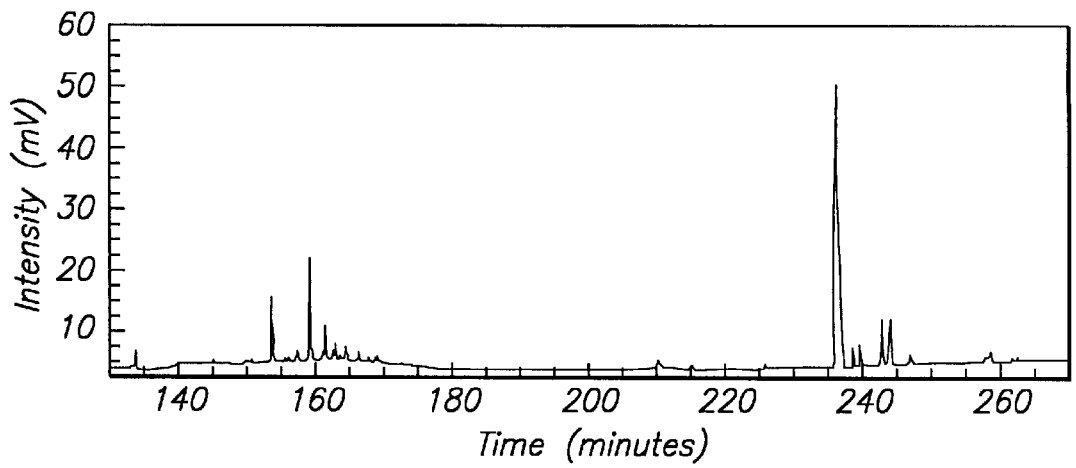
FIG. 6a shows in chromatographic form the product of the first hydroisomerization run, performed at 420° F., as described in Example 5.
Figure 6B:
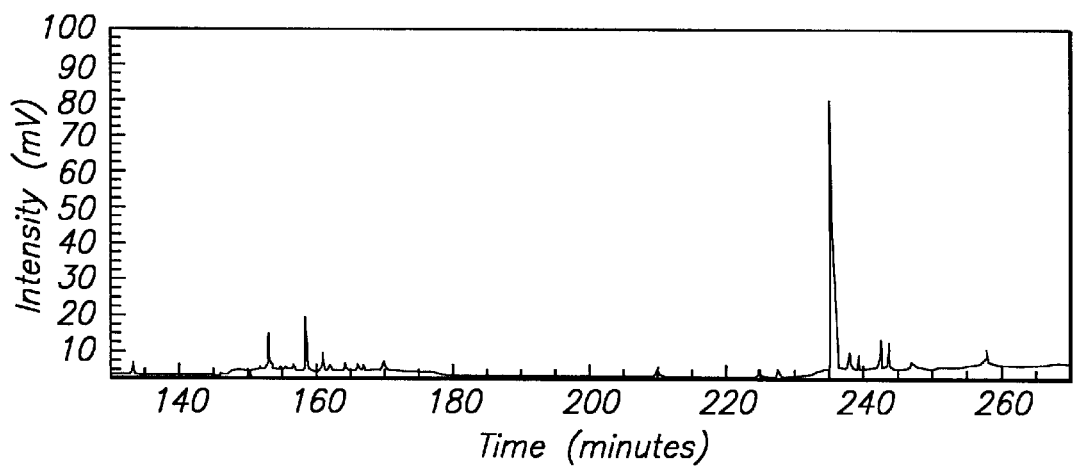
FIG. 6b shows in chromatographic form the product of the second hydroisomerization run, performed at 400° F., as also described in Example 5.
Figure 6C:
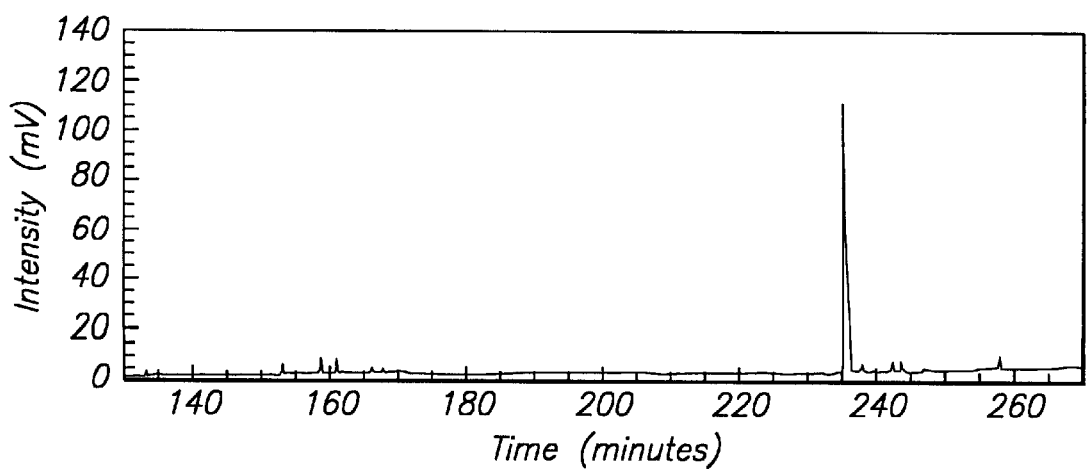
FIG. 6c shows in chromatographic form the product of the third hydroisomerization run, performed at 350° F., as also described in Example 5.
Figure 7A:
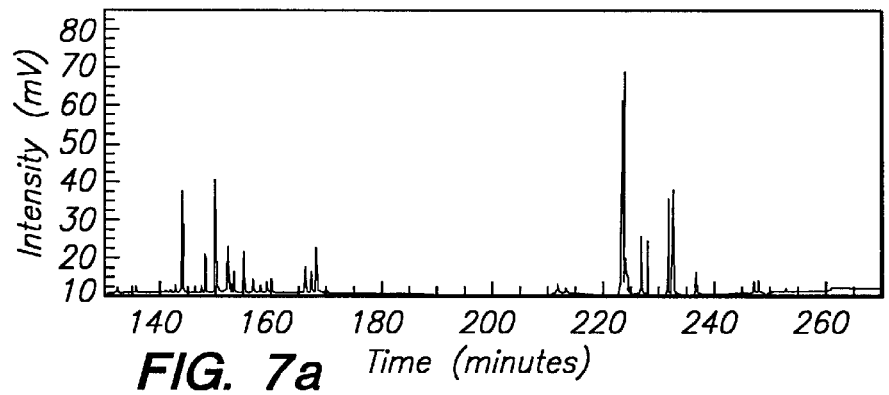
FIG. 7a shows in chromatographic form the product of the first hydroisomerization run, performed at 440° F., as described in Example 6.
Figure 7B:
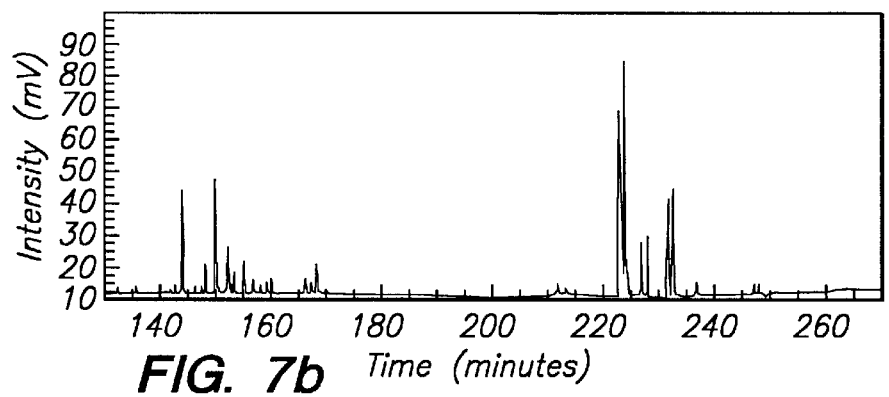
FIG. 7b shows in chromatographic form the product of the second hydroisomerization run, performed at 420° F., as also described in Example 6.
Figure 7C:
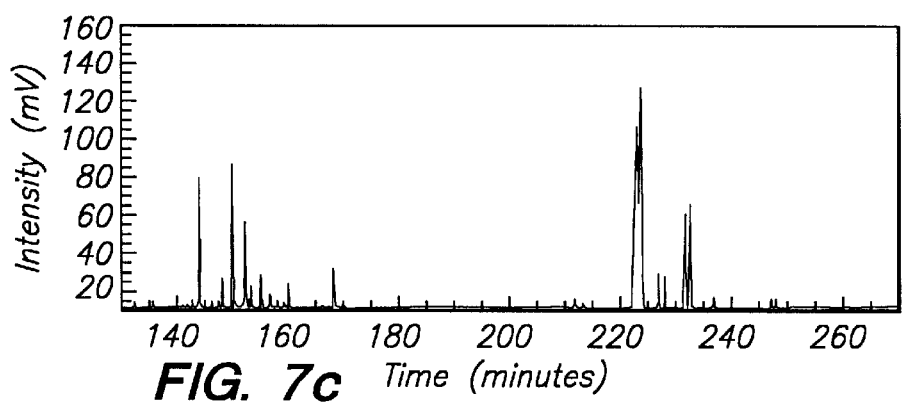
FIG. 7c shows in chromatographic form the product of the third hydroisomerization run, performed at 400° F., as also described in Example 6.
Figure 7D:
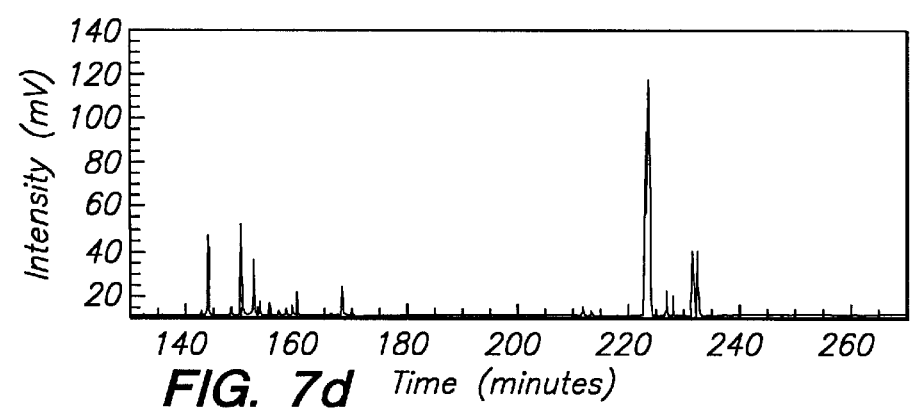
FIG. 7d shows in chromatographic form the product of the fourth hydroisomerization run, performed at 380° F., as also described in Example 6.

Three experiments were performed to hydroisomerize a hydrocarbon feed of 5:1 (wt:wt) o-xylene: 2,7-dimethylnaphthalene in a reactor with PdSN to produce DMT's and DMN's at 420, 400 and 350° F., respectively. Other conditions were 200 psig, 1 ml/hr feed, 40 ml/min $H_2$ and 0.5 g catalyst. The composition of the feed is shown in chromatographic form in FIG. 10a (see Example 8). The results obtained at 420, 400 and 350° F. are shown in chromatographic form in FIGS. 6a, 6b and 6c, respectively. The compositions of the products are given in weight % in Table V. No methyinaphthalenes were detected. Essentially no cracking products were observed.

TABLE V

| Temperature (° F.) | 420 | 400 | 350 |
|---|---|---|---|
| DMN's | 3.1 | 2.9 | 2.6 |
| DMD's + other C12's | 33.2 | 23.5 | 9.0 |
| DMT's (total) | 63.7 | 73.6 | 88.4 |
| 1,5-DMT | 0.4 | 0.2 | 0 |
| 1,6-DMT | 1.8 | 1.1 | 0.2 |
| 2,5-DMT | 4.6 | 3.6 | 0.9 |

TABLE V-continued

| 1,7-DMT | 2.1 | 1.8 | 1.1 |
|---|---|---|---|
| 2,8-DMT | 4.3 | 3.8 | 1.3 |
| 2,7-DMT | 29.8 | 45.3 | 78.9 |
| 2,6-DMT | 20.1 | 17.4 | 5.8 |
| 1,4-DMT | 0 | 0 | 0 |
| Other DMT's | 0.6 | 0.4 | 0.2 |

Example 6

Hydroisomerization of 2,7-DMN with PdS/Y

Figure 8:
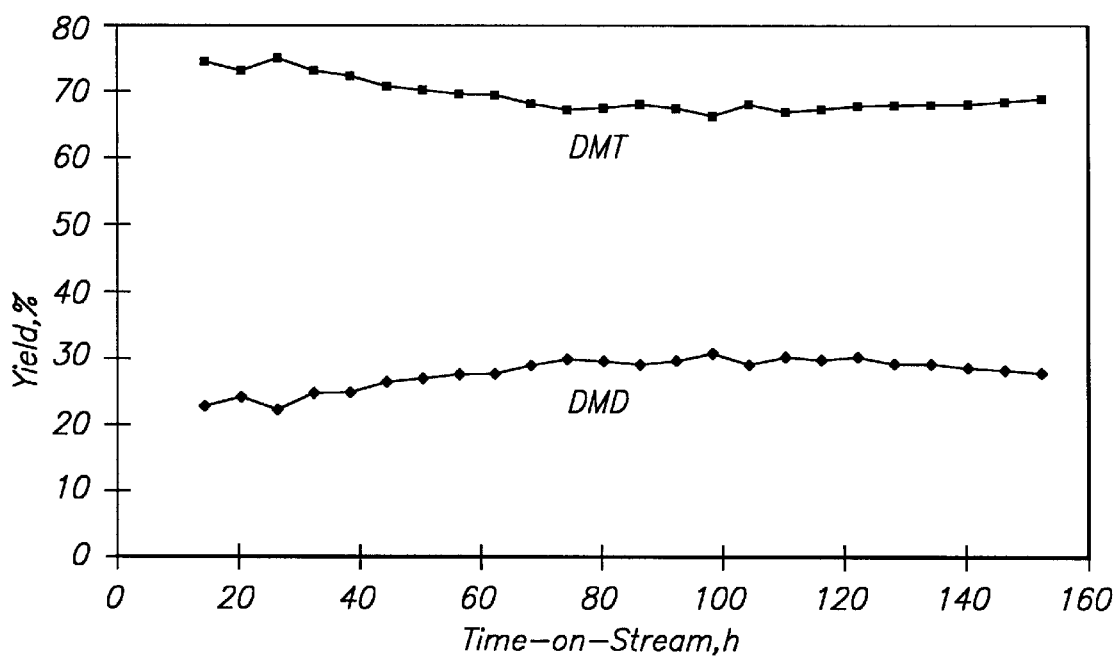
FIG. 8 is a graph plotting the yields of DMT and DMD products resulting from the hydroisomerization run of 2,7-DMN at 400° F. versus the time-on-stream at which the products were analyzed on-line as described in Example 6.

Four experiments were performed to hydroisomerize a hydrocarbon feed of 5:1 (wt:wt) o-xylene: 2,7-dimethylnaphthalene in a reactor with PdS/Y at 500 psig, 1 ml/hr feed, 40 ml/min $H_2$ and 0.5 g catalyst. The reaction temperature was 380, 400, 420 and 440° F., respectively. The composition of the 2,7-DMN feed is shown in chromatographic form in FIG. 10a (see Example 8). The results obtained at these four temperatures are shown in chromatographic form in FIGS. 7a, 7b, 7c and 7d, respectively. The detailed GC peak identification is demonstrated in FIGS. 1a, 1b, 2a, 2b, 3a, 3b, 4a, 4b, 5a, 5b, 10a and 10b. The compositions of the products are given in weight % in Table VI. No methylnaphthalenes were detected. Essentially no cracking products were observed. FIG. 8 demonstrates the DMT and DMD yields versus the reaction time for the run at 400° F. After an initial period of about 70 hours, the catalyst activity and selectivity became stable. For the next two weeks, this catalyst in the same reactor was uninterruptedly screened under various conditions with various feeds containing various DMN isomers. The results indicate no apparent deactivation of the catalyst.

TABLE VI

| Temperature (° F.) | 440 | 420 | 400 | 380 |
|---|---|---|---|---|
| DMN's | 1.9 | 1.3 | 0.3 | 0.2 |
| DMD's + other C12's | 38.3 | 34.4 | 31.1 | 19.9 |
| DMT's (total) | 59.8 | 64.3 | 68.6 | 79.9 |
| 1,5-DMT | 1.1 | 0.8 | 0.3 | 0.1 |
| 1,6-DMT | 3.5 | 3.0 | 1.3 | 1.0 |
| 2,5-DMT | 6.5 | 6.5 | 6.0 | 4.4 |
| 1,7-DMT | 3.5 | 3.1 | 1.5 | 1.5 |
| 2,8-DMT | 6.3 | 6.5 | 5.9 | 4.8 |
| 2,7-DMT | 18.8 | 23.3 | 33.4 | 49.5 |
| 2,6-DMT | 17.7 | 19.6 | 20.1 | 18.6 |
| 1,4-DMT | 0 | 0 | 0 | 0 |
| Other DMT's | 2.4 | 1.5 | 0.1 | 0 |

Example 7

Hydroisomerization of 2,7-DMN with PdS/Y

Figure 9A:
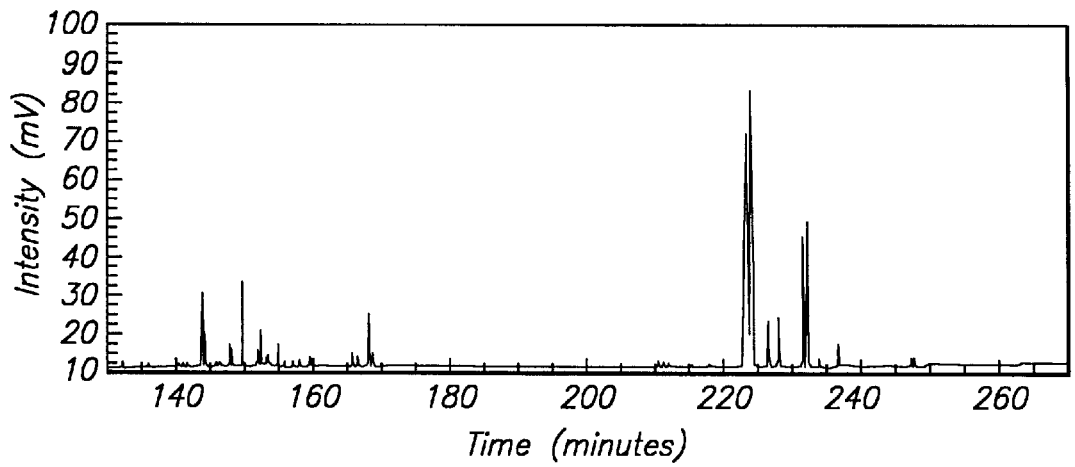
FIG. 9a shows in chromatographic form the product of the first hydroisomerization run, performed at 440° F., as described in Example 7.
Figure 9B:
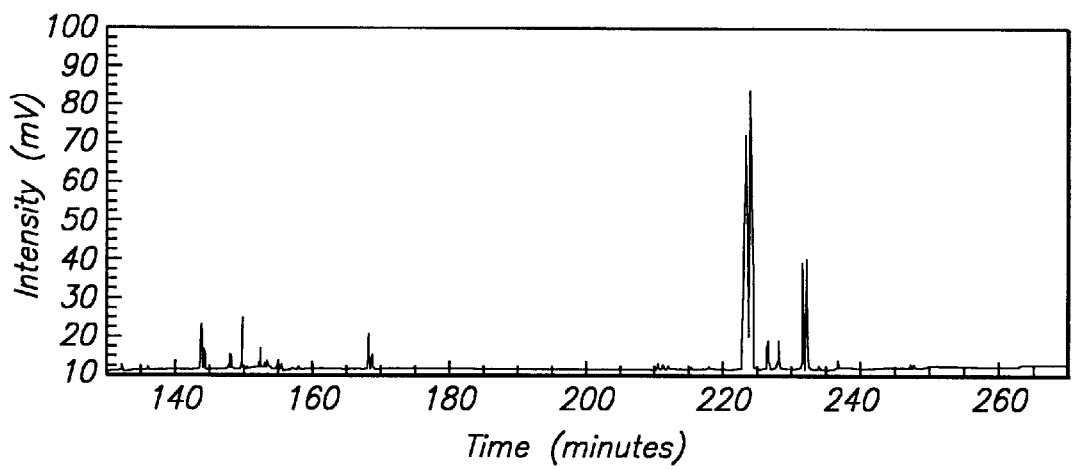
FIG. 9b shows in chromatographic form the product of the second hydroisomerization run, performed at 420° F., as also described in Example 7.
Figure 9C:
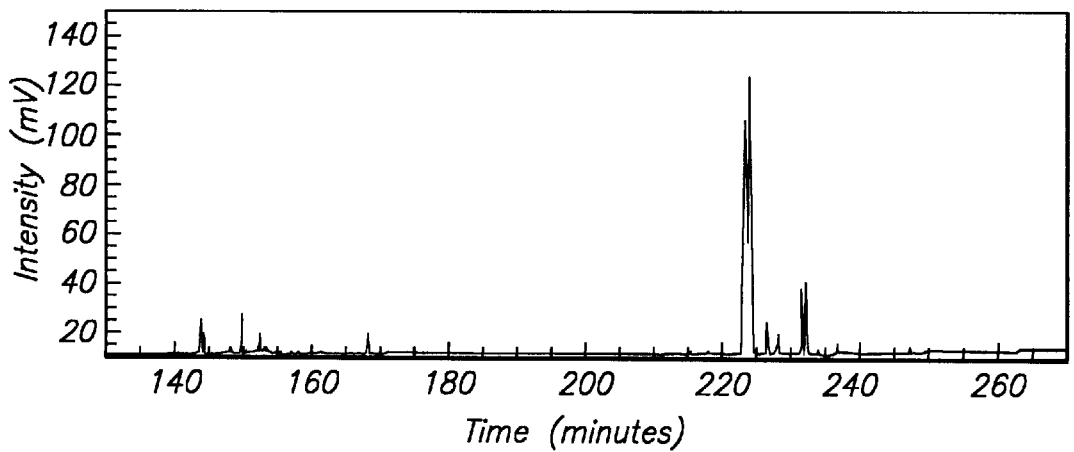
FIG. 9c shows in chromatographic form the product of the third hydroisomerization run, performed at 400° F., as also described in Example 7.

Three experiments were performed to hydroisomerize a hydrocarbon feed of 5:1 (wt:wt) o-xylene: 2,7-dimethylnaphthalene in a reactor with PdS/Y at 500 psig, 2 ml/hr feed, 40 ml/min and 0.5 g catalyst. The reaction temperature was 400, 420 and 440° F., respectively. The composition of the 2,7-DMN feed is shown in chromatographic form in FIG. 10a (see Example 8). The results obtained at these three temperatures are shown in chromatographic form in FIGS. 9a, 9b and 9c, respectively. The detailed GC peak identification is demonstrated in FIGS. 1a, 1b, 2a, 2b, 3a, 3b, 4a, 4b, 5a, 5b, 10a and 10b. The compositions of the products are given in weight % in Table VII. No methylnaphthalenes were detected. Essentially no cracking products were observed.

TABLE VII

| Temperature (° F.) | 440 | 420 | 400 |
|---|---|---|---|
| DMN's | 1.4 | 1.0 | 1.7 |
| DMD's + other C12's | 22.5 | 12.2 | 7.5 |
| DMT's(total) | 76.1 | 86.8 | 90.8 |
| 1,5-DMT | 0.9 | 0.4 | 0.2 |
| 1,6-DMT | 2.9 | 1.7 | 0.9 |
| 2,5-DMT | 8.7 | 7.0 | 4.3 |
| 1,7-DMT | 2.9 | 1.9 | 1.7 |
| 2,8-DMT | 8.3 | 7.1 | 4.7 |
| 2,7-DMT | 26.3 | 42.3 | 61.0 |
| 2,6-DMT | 24.4 | 26.0 | 17.8 |
| 1,4-DMT | 0 | 0 | 0 |
| Other DMT's | 1.7 | 0.4 | 0.2 |

Example 8

Hydroisomerization of 2,7-DMN with Pd/B/Al/Beta

An experiment was performed to isomerize a hydrocarbon feed of 5:1 (wt:wt) o-xylene: 2,7-dimethylnaphthalene in a reactor with a Pd/Boron-Beta catalyst (0.5 g) containing 500 ppm aluminum. The reaction conditions were: 475° F., 200 psig, 1 ml/hr feed, 40 ml/min $H_2$. The 2,7-DMN feed used in the experiment is shown in chromatographic form in FIG. 10a. The result of the experiment is shown in chromatographic form in FIG. 10b. 89.2% of the product was DMT's. 8.7% of the product was DMD's and others. 2.1% of the product was DMN's.

Example 9

Hydroisomerization of 2,7-DMN with PdS/SAPO-11

Several experiments were made to hydroisomerize a hydrocarbon feed of 5:1 (wt:wt) o-xylene: 2,7-dimethylnaphthalene in a reactor with a PdS/SAPO-11 (0.5 g) with 40 ml/min $H_2$ at a feed rate of 1 ml/hr. The results are shown in weight % in Tables IXa-IXc.

TABLE IXa

| | Experiment 1 | Experiment 2 | Experiment 3 | Experiment 4 |
|---|---|---|---|---|
| Temperature (° F.) | 650 | 600 | 500 | 650 |
| Pressure (psig) | 200 | 200 | 200 | 100 |
| WHSV($h^{-1}$) | 2 | 2 | 2 | 2 |
| DMD's | 13.0 | 45.2 | 100 | 14.2 |
| DMT's | 34.5 | 34.4 | | 19.3 |
| DMN (total) | 52.0 | 20.4 | | 65.9 |
| 2,7-DMN | 24.9 | 11.1 | | 46.5 |
| 1,7-DMN | 6.2 | 1.9 | | 6.1 |
| 1,8-DMN | 0 | 0 | | 0 |
| 2,6-DMN | 14.5 | 5.7 | | 10.5 |
| 1,6-DMN | 6.2 | 1.6 | | 2.7 |
| 1,5-DMN | 0.2 | 0.1 | | 0.1 |
| 1,3-DMN | 0 | 0 | | 0 |
| 2,3-DMN | 0 | 0 | | 0 |
| 1,4-DMN | 0 | 0 | | 0 |
| 1,2-DMN | 0 | 0 | | 0 |
| MN's | ~0.5 | ~0.6 | | ~0.3 |
| TMN's | 0 | 0 | | ~0.1 |

DMN: dimethylnaphthalene; DMT: dimethyltetralin; DMD: dimethyldecalin; MN: methylnaphthalene; TMN: trimethylnaphthalene.

TABLE IXb

| | Experiment 5 | Experiment 6 | Experiment 7 | Experiment 8 |
|---|---|---|---|---|
| Temperature (° F.) | 700 | 725 | 725 | 725 |
| Pressure (psig) | 200 | 200 | 150 | 150 |
| WHSV($h^{-1}$) | 6 | 6 | 6 | 6 |
| DMD's | 2.1 | 1.4 | 0.3 | trace |
| DMT's | 20.3 | 13.7 | 8.3 | ~9 |
| DMN (total) | 77.2 | 84.4 | 90.9 | 90.5 |
| 2,7-DMN | 50.5 | 55.0 | ~70 | ~70 |
| 1,7-DMN | 9.6 | 14.6 | 15.4 | 15.4 |
| 1,8-DMN | 0 | 0 | 0 | 0 |
| 2,6-DMN | 13.2 | 9.7 | ~3 | ~3 |
| 1,6-DMN | 3.8 | 4.8 | 2.4 | 2.0 |
| 1,5-DMN | 0.1 | 0.3 | 0.1 | 0.1 |
| 1,3-DMN | 0 | 0 | 0 | 0 |
| 2,3-DMN | 0 | 0 | 0 | 0 |
| 1,4-DMN | 0 | 0 | 0 | 0 |
| 1,2-DMN | 0 | 0 | 0 | 0 |
| MN's | ~0.3 | ~0.5 | ~0.4 | ~0.3 |
| TMN's | ~0.1 | 0 | ~0.1 | 0 |

TABLE IXc

| | Experiment 9 | Experiment 10 | Experiment 11 | Experiment 11 (reanalyzed) |
|---|---|---|---|---|
| Temperature (° F.) | 725 | 725 | 775 | 775 |
| Pressure (psig) | 150 | 150 | 150 | 150 |
| WHSV ($h^{-1}$) | 12 | 2 | 2 | 2 |
| DMD's | trace | trace | trace | 0.7 |
| DMT's | ~8 | 8.0 | 5.2 | 4.6 |
| DMN (total) | 93.0 | 92.0 | 93.6 | 93.7 |
| 2,7-DMN | ~80 | 55.5 | 45.5 | 44.7 |
| 1,7-DMN | ~12 | 21.3 | 31.7 | 32.1 |
| 1,8-DMN | 0 | 0 | 0 | 0 |
| 2,6-DMN | trace | 8.4 | 8.2 | 8.9 |
| 1,6-DMN | ~1 | 6.5 | 7.4 | 7.5 |
| 1,5-DMN | 0 | 0.3 | 0.8 | 0.5 |
| 1,3-DMN | 0 | 0 | 0 | 0 |
| 2,3-DMN | 0 | 0 | 0 | 0 |
| 1,4-DMN | 0 | 0 | 0 | 0 |
| 1,2-DMN | 0 | 0 | trace | 0 |
| MN's | 0 | trace | ~0.9 | 0.9 |
| TMN's (wt %) | 0 | 0 | 0.3 | 0.1 |

Example 10

GC/MS Analysis of Products of Hydroisomerization of 2,7-DMN with PdS/SAPO-11

Gas chromatography coupled with mass spectrometry was used to identify the products from a particular yield period (Experiment 5 in Example 9). The composition of the products from Experiment 5 at 700° F., 200 psig, 6 $h^{-1}$ WHSV is listed in weight % in Tables Xa and Xb. The difference between the compositions determined by on-line GC (see Table IXb) and off-line GC/MS (see Tables Xa and Xb) is apparently due to the different sensitivity of these two different analytical techniques.

TABLE Xa

| DMD's | $C_3I$'s | DMT's | MN's | $C_6Bz + C_5Tol$ |
|---|---|---|---|---|
| 2.3 | 3.4 | 21.0 | 0.6 | 0.8 |

TABLE Xb

| 2,7-DMN | 1,7-DMN | 2,6-DMN | 1,6-DMN | 1,5-DMN |
|---|---|---|---|---|
| ~45.5 | 10.5 | ~11 | 4.2 | 0.2 |

Acid Catalyst Isomerization without Hydrogenation

Example 11 shows the results of an experiment in which an acid catalyst is used without combining it with a hydrogenating catalyst.

Example 11

Isomerization of 2,7-DMN with H-ZSM-11

Figure 11A:
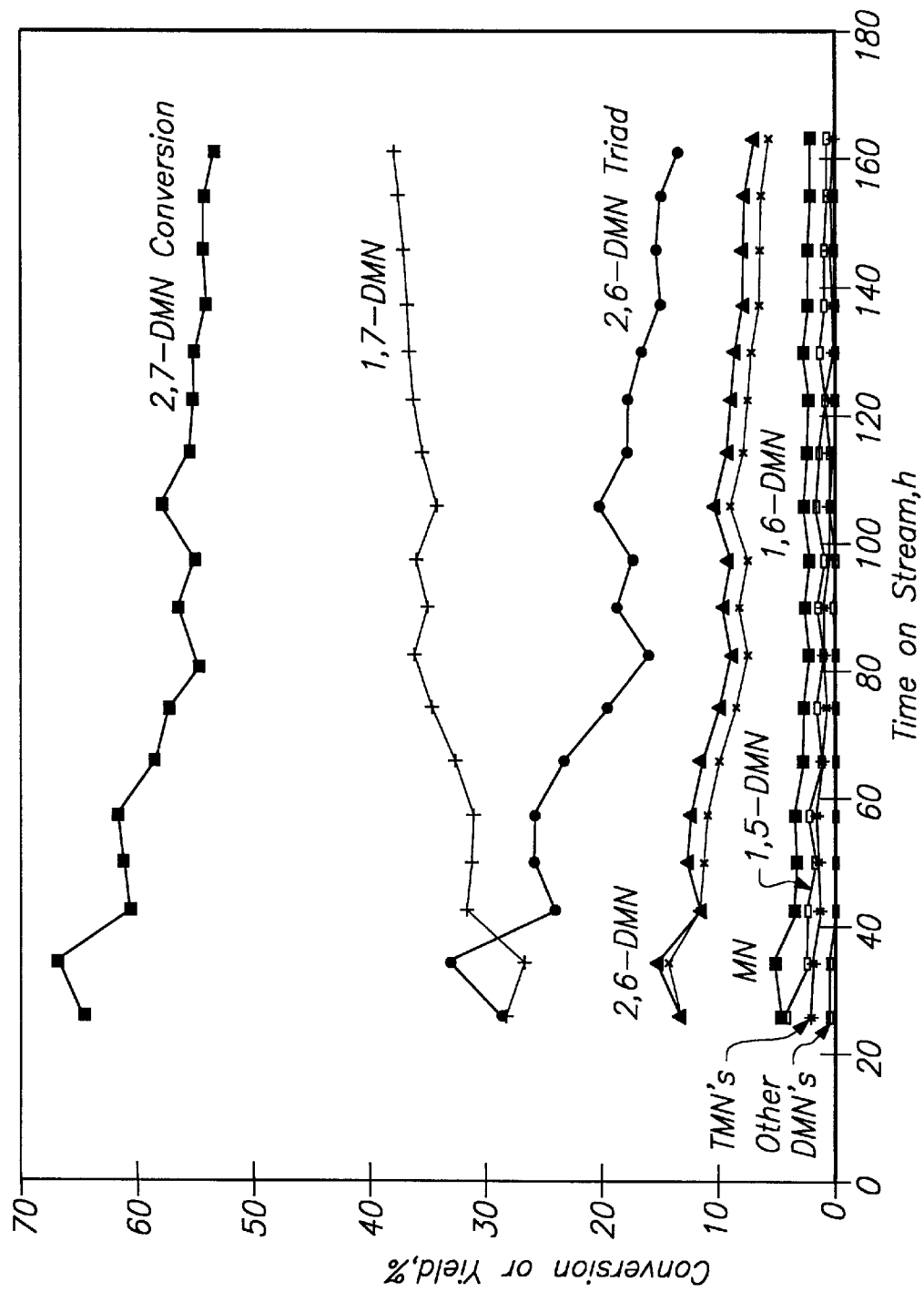
FIG. 11a is a graph plotting the conversion of 2,7-DMN and yields of various products resulting from an acid-catalyzed isomerization of 2,7-DMN on H-ZSM-11 versus the time-on-stream, as described in Example 11.
Figure 11B:
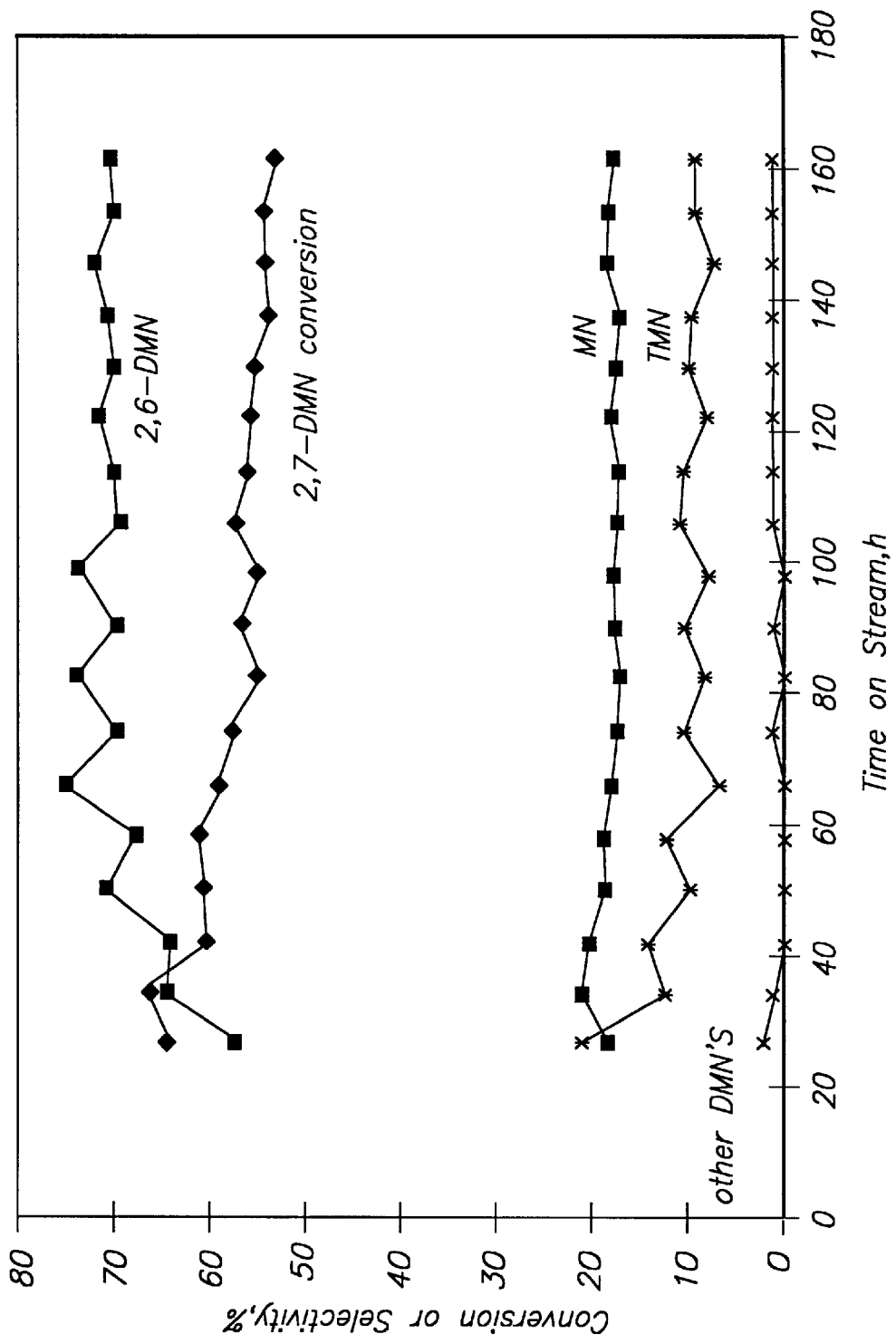
FIG. 11b is a similar graph plotting the conversion and selectivities versus the time-on-stream when the resulting 1,5-, 1,6- and 1,7-DMN as well as the unconverted 2,7-DMN are assumed to be recycled and finally converted to 2,6-DMN.

An experiment was performed to isomerize a hydrocarbon feed of 5:1 (wt:wt) o-xylene: 2,7-dimethylnaphthalene in a reactor with an acid catalyst, H-ZSM-11 with no carrier gas at 600° F., ~5 psig, 1 ml/hr feed and 0.2 h$^{-1}$ WHSV. The results are shown in graphic form in FIG. 11a. Assuming that the resulting 1,5-, 1,6- and 1,7-DMN as well as the unconverted 2,7-DMN are recyclable and can be finally converted to 2,6-DMN, the selectivities of the desirable 2,6-DMN and other major by-products such as MN's and TMN's then can be depicted as shown in FIG. 11 b. It is apparent that this kind of acid-catalyzed DMN isomerization results in a significant amount of by-products such as MN's (methylnaphthalenes) and TMN's (trimethylnaphthalenes) that can be depicted as shown in FIG. 11b.

Hydroisomerization/Dehydrogenation

Examples 12–25 describe experiments in which product of the hydroisomerization step is then dehydrogenated with a separate catalyst.

Example 12

Hydroisomerization/Dehydrogenation of 2,7-DMN with PdS/SAPO-11 and PtS/Cs/B-SSZ-42

Experiments were conducted using a two-reactor hydroisomerization/dehydrogenation system. The first reactor facilitates the hydroisomerization function and the second reactor performs the function of dehydrogenating saturated compounds back to DMN's. In the first reactor, a PdS/SAPO-11 catalyst (0.5 g) was used. In the second reactor, a PtS/Cs/Boron-SSZ-42 (0.45 g) catalyst was used. Tables XIIa and XIIb show results from using the two reactor system. The feed was composed of o-xylene and 2,7-DMN in a 5:1 (wt:wt) ratio.

TABLE XIIa

|  | Experiment 1 | | Experiment 2 | |
|---|---|---|---|---|
|  | Reactor 1 | Reactor 2 | Reactor 1 | Reactor 2 |
| Temperature, ° F. | 650 | 750 | 650 | 795 |
| Pressure, psig | 200 | ~5 | 200 | ~5 |
| Feed Rate, ml/hr | 1 | 1 | 1 | 1 |
| H$_2$ Rate, ml/min | 40 | 40 | 40 | 40 |
| C$_5^-$ | <1 | ~0 | <1 | ~0 |
| DMD's | 12.7 | 3.2 | 12.0 | 2.1 |
| DMT's, C$_3$I's MN's | 38.2 | 4.8 | 38.2 | 4.7 |
| DMN's (total) | 48.1 | 92.0 | 48.8 | 93.2 |
| 2,7-DMN |  | 68.7 |  | 69.2 |
| 1,7-DMN |  | 8.1 |  | 8.5 |

TABLE XIIa-continued

|  | Experiment 1 | | Experiment 2 | |
|---|---|---|---|---|
|  | Reactor 1 | Reactor 2 | Reactor 1 | Reactor 2 |
| 2,6-DMN |  | 12.6 |  | 12.6 |
| 1,6-DMN |  | 2.6 |  | 2.5 |
| 1,5-DMN |  | ~0 |  | ~0 |
| Other DMN's |  | ~0 |  | ~0 |

DMN: dimethylnaphthalene; DMT: dimethyltetralin; DMD: dimethyldecalin; MN: methylnaphthalene; C$_3$I: indan substituted with a C$_3$ alkyl group.

TABLE XIIb

|  | Experiment 3 | | Experiment 4 | |
|---|---|---|---|---|
|  | Reactor 1 | Reactor 2 | Reactor 1 | Reactor 2 |
| Temperature, ° F. | 650 | 900 | 725 | 800 |
| Pressure, psig | 200 | ~5 | 400 | ~5 |
| Feed Rate, ml/hr | 1 | 1 | 0.5 | 0.5 |
| H$_2$ Rate, ml/min | 40 | 40 | 30 | 30 |
| C$_5^-$ | <1 | ~0 | ~5 | ~0 |
| DMD's | 11.1 | 0.6 | 14.9 | 5.3 |
| DMT's, C$_3$I's, MN's | 39.0 | 5.2 | 39.6 | 22.7 |
| DMN's (total) | 48.9 | 94.2 | 40.3 | 72.0 |
| 2,7-DMN |  | 70.2 |  | 32.2 |
| 1,7-DMN |  | 9.0 |  | 12.7 |
| 2,6-DMN |  | 12.4 |  | 17.1 |
| 1,6-DMN |  | 2.6 |  | 10.0 |
| 1,5-DMN |  | ~0 |  | ~0 |
| Other DMN's |  | ~0 |  | ~0 |

Example 13

GC/MS Analysis of Products of Hydroisomerization/Dehydrogenation of 2,7-DMN with PdS/SAPO-11 and PtS/Cs/B-SSZ-42

Gas chromatography (GC) coupled with mass spectrometry (MS) was used to identify the products from particular yield periods (shown in Example 12) after Reactor 2. The distributions of different non-DMN's in the non-DMN products are listed in weight % in Table XIII based on the GC/MS results.

TABLE XIII

|  | Experiment 1 | Experiment 2 | Experiment 3 | Experiment 4 |
|---|---|---|---|---|
| MI's | — | 1.9 | 9.1 | — |
| EI's | — | — | 4.8 | 0.8 |
| DMD's | 39.5 | 30.8 | 9.4 | 19.0 |
| DMT's | 28.3 | 29.1 | 6.8 | 34.1 |
| MEI's | 3.5 | 3.8 | — | — |
| MEI⁻'s | 11.0 | 12.3 | 17.2 | 13.6 |
| MN's | 10.1 | 14.8 | 43.8 | 6.1 |
| C$_5$Tol's | 7.6 | 7.3 | 8.9 | 24.9 |
| EN's | — | — | — | 1.5 |

MI: methylindan; EI: ethylindan; DMD: dimethyldecalin; DMT: dimethyltetralin; MEI: methylethylindan; MEI⁻: methylethylindene; MN: methylnaphthalene; C$_5$TOl: toluene substituted with a C$_5$ alkyl group; EN: ethylnaphthalene.

Example 14

Hydroisomerization/Dehydrogenation of 2,7-DMN with Pd/B/Al/Beta and PtS/Cs/B-SSZ-42

Experiments were conducted using a two-reactor hydroisomerization/dehydrogenation system. The first reactor facilitates the hydroisomerization function and the second reactor performs the function of dehydrogenating saturated compounds back to DMN's. In the first reactor, a Pd/Boron/500 ppm Al/beta catalyst (0.5) was used. In the second reactor, a PtS/Cs/Boron-SSZ-42 (0.45 g) catalyst was used. Table XIV shows results for the example. In this example, the feed was composed of o-xylene and 2,7-DMN of a 5:1 wt:wt ratio. The slightly high yield of MN's after reactor 2 is likely related to the dealkylation of the resulting DMN's on PtS/Cs/B-SSZ-42.

TABLE XIV

|  | Experiment 1 | | Experiment 2 | | Experiment 3 | |
| --- | --- | --- | --- | --- | --- | --- |
|  | Reactor 1 | Reactor 2 | Reactor 1 | Reactor 2 | Reactor 1 | Reactor 2 |
| Temperature, °F. | 535 | 850 | 500 | 850 | 475 | 850 |
| Pressure, psig | 200 | ~5 | 200 | ~5 | 200 | ~5 |
| Feed Rate, ml/hr | 1 | 1 | 1 | 1 | 1 | 1 |
| $H_2$ Rate, ml/min | 40 | 40 | 40 | 40 | 40 | 40 |
| $C_5^-$ | 1.8 | — | ~0.6 | — | <0.3 | — |
| DMD's | 20.1 | 12.4 | 13.7 | 4.3 | 9.6 | 1.7 |
| DMT's, $C_3I$'s | 72.7 | 17.2 | 84.2 | 4.2 | 89.4 | 2.0 |
| MN's | ~0 | 3.3 | ~0 | 3.0 | ~0 | 3.7 |
| DMN's (total) | 5.4 | 67.1 | 1.5 | 86.9 | 0.7 | 92.6 |
| 2,7-DMN |  | 21.0 |  | 32.1 |  | 41.3 |
| 1,7-DMN |  | 11.3 |  | 10.2 |  | 6.9 |
| 2,6-DMN |  | 20.6 |  | 31.1 |  | 34.4 |
| 1,6-DMN |  | 13.0 |  | 12.8 |  | 10.0 |
| 1,5-DMN |  | 0.9 |  | 0.4 |  | — |
| Other DMN's |  | 0.3 |  | 0.3 |  | — |

DMN: dimethylnaphthalene; DMT: dimethyltetralin; DMD: dimethyldecalin; MN: methylnaphthalene; $C_3I$: indan substituted with a $C_3$ alkyl group.

Example 15

Hydroisomerization/Dehydrogenation of 2,7-DMN with Pd/B/Al/Beta and PtS/Cs/B-SSZ-42

Further experiments were conducted using a two-reactor hydroisomerization/dehydrogenation system similar to Example 14. The first reactor facilitates the hydroisomerization function and the second reactor performs the function of dehydrogenating saturated compounds back to DMN's. In the first reactor, a Pd/Boron/500 ppm Al/beta catalyst (0.5 g) was used. In the second reactor, a PtS/Cs/Boron-SSZ-42 (0.45 g) catalyst was used. Table XV shows results for the example. In this example, the feed was composed of o-xylene and 2,7-DMN of a 5:1 wt:wt ratio. As described in Example 14, the slightly high yield of MN's after reactor 2 is likely related to the dealkylation of the resulting DMN's on PtS/Cs/B-SSZ-42.

TABLE XV

|  | Experiment 1 | | Experiment 2 | |
| --- | --- | --- | --- | --- |
|  | Reactor 1 | Reactor 2 | Reactor 1 | Reactor 2 |
| Temperature, °F. | 475 | 850 | 475 | 850 |
| Pressure, psig | 200 | ~5 | 200 | ~5 |
| Feed Rate, ml/hr | 1.3 | 1.3 | 1.1 | 1.1 |
| $H_2$ Rate, ml/min | 40 | 40 | 40 | 40 |
| $C_5^-$ | <1 | — | — | — |
| DMD's | 5.0 | 0.9 | 2.7 | 0.8 |

TABLE XV-continued

|  | Experiment 1 | | Experiment 2 | |
| --- | --- | --- | --- | --- |
|  | Reactor 1 | Reactor 2 | Reactor 1 | Reactor 2 |
| DMT's, $C_3I$'s | 94.2 | 1.5 | 96.3 | 2.0 |
| MN's | ~0 | 2.5 | ~0 | 5.3 |
| DMN's (total) | 0.7 | 95.1 | <1 | 91.9 |
| 2,7-DMN |  | 51.5 |  | 42.4 |
| 1,7-DMN |  | 4.8 |  | 6.7 |
| 2,6-DMN |  | 32.0 |  | 33.4 |
| 1,6-DMN |  | 6.8 |  | 9.4 |
| 1,5-DMN |  | ~0 |  | ~0 |
| Other DMN's |  | ~0 |  | ~0 |

DMN: dimethylnaphthalene; DMT: dimethyltetralin; DMD: dimethyldecalin; MN: methylnaphthalene; $C_3I$: indan substituted with a $C_3$ alkyl group.

Example 16

GC/MS Analysis of Products of Hydroisomerization/Dehydrogenation of 2,7-DMN with Pd/B/Al/Beta and PtS/Cs/B-SSZ-42

Gas chromatography coupled with mass spectrometry was used to identify some of the products obtained from Example 15 described. The product from Experiment 1 of Example 15 was collected from Reactor 1 only and is designated in this example as Experiment A. The product from Experiment 2 of Example 15 was collected from both Reactors 1 and 2 and is designated in this example as Experiment B. The results of the identification of the products from both experiments in weight % are shown in Table XVI. The difference between the compositions determined by GC (see Table XV of Example 15) and GC/MS (see Table XVI of this example) is apparently due to the different sensitivities of these two different analytical techniques.

TABLE XVI

|  | Experiment A (reactor 1 only) | Experiment B (reactors 1 + 2) |
| --- | --- | --- |
| N (naphthalene) | 0 | 0.2 |
| MI's (methylindans) | 0 | 0.2 |
| EI's (ethylindans) or DMI's (dimethylindans) | 0 | 0.3 |
| DMD's (dimethyldecalins) | 13.5 | 1.4 |
| DMT's (dimethyltetralins) | 78.1 | 2.7 |
| MEI's (methylethylindansy or TMI's (trimethylindans) | 4.5 | 0.2 |
| MEI⁻'s (methylethylindenes) | 0 | 0 |
| MN's (methylnaphthalenes) | 0 | 7.0 |
| $C_5$Tol's ($C_5$-toluenes) | 1.0 | 0 |
| EN's (ethylnaphthalenes) | 0 | 0.2 |
| DMN's (dimethylnaphthalenes) | 2.5 | 87.1 |
| TMT's (trimethyltetralins) | 0.4 | 0 |
| TMN's (trimethylnaphthalenes) | 0 | 0.7 |

Example 17

Hydroisomerization/Dehydrogenation of 2,7-DMN with PdS/Siral 40 and PtS/Cs/B-SSZ-42

Experiments were conducted using a two-reactor hydroisomerization/dehydrogenation system. The first reactor facilitates the hydroisomerization function and the second reactor performs the function of dehydrogenating saturated compounds back to DMN's. In the first reactor, a PdS/Siral 40 catalyst, consisting of sulfided Pd deposited on commercial Siral 40 silica-alumina (0.5 g), was used. In the second reactor, a PtS/Cs/Boron-SSZ-42 (0.45 g) catalyst was used. Tables XVIIa and XVIIb show results in weight % for the experiments. In these experiments, the feed was composed of o-xylene and 2,7-DMN in a 5:1 (wt:wt) ratio.

TABLE XVIIa

|  | Experiment 1 | | Experiment 2 | |
| --- | --- | --- | --- | --- |
|  | Reactor 1 | Reactor 2 | Reactor 1 | Reactor 2 |
| Temperature, °F. | 550 | 850 | 500 | 850 |
| Pressure, psig | 200 | ~5 | 200 | ~5 |
| Feed Rate, ml/hr | 1 | 1 | 1 | 1 |
| $H_2$ Rate, ml/min | 40 | 40 | 40 | 40 |
| $C_5$- | ~1.2 | — | ~0.7 | — |
| DMD's | 55.8 | 22.5 | 42.9 | 13.4 |
| DMT's, $C_3I$'s | 38.8 | 13.2 | 54.7 | 6.7 |
| MN's | ~0 | 2.6 | ~0 | 3.7 |
| DMN's (total) | 4.1 | 61.7 | 1.7 | 76.2 |
| 2,7-DMN |  | 28.5 |  | 39.2 |
| 1,7-DMN |  | 5.5 |  | 8.1 |
| 2,6-DMN |  | 18.6 |  | 19.5 |
| 1,6-DMN |  | 6.7 |  | 8.4 |
| 1,5-DMN |  | 0.5 |  | 0.5 |
| Other DMN's |  | 1.9 |  | 0.5 |
|  |  | (2,3- & 1,2-DMN) |  | (2,3- & 1,2-DMN) (also 0.3 TMN's) |

DMN: dimethylnaphthalene; DMT: dimethyltetralin; DMD: dimethyldecalin; MN: methylnaphthalene; $C_3I$: indane with a $C_3$ alkyl group; TMN: trimethylnaphthalene.

TABLE XVIIb

|  | Experiment 3 | | Experiment 4 | |
| --- | --- | --- | --- | --- |
|  | Reactor 1 | Reactor 2 | Reactor 1 | Reactor 2 |
| Temperature, °F. | 500 | 850 | 475 | 850 |
| Pressure, psig | 200 | ~5 | 200 | ~5 |
| Feed Rate, ml/hr | 1 | 1 | 1 | 1 |
| $H_2$ Rate, ml/min | 40 | 40 | 40 | 40 |
| $C_5$- | ~0.3 | — | ~0.4 | — |
| DMD's | 28.9 | 7.7 | 27.0 | 5.5 |
| DMT's, $C_3I$'s | 69.4 | 2.0 | 71.8 | 1.4 |
| MN's | ~0 | 4.2 | ~0 | 5.1 |
| DMN's (total) | 1.4 | 86.1 | 0.8 | 88.0 |
| 2,7-DMN |  | 47.9 |  | 59.4 |
| 1,7-DMN |  | 7.1 |  | 4.7 |
| 2,6-DMN |  | 24.6 |  | 19.6 |
| 1,6-DMN |  | 6.5 |  | 4.1 |
| 1,5-DMN |  | — |  | 0.2 |
| Other DMN's |  | — |  | trace |

Example 18

Hydroisomerization/dehydrogenation of 2,7-DMN with Pd/B/Al/Beta and PtS/Na-ZSM-5

Figure 12A:
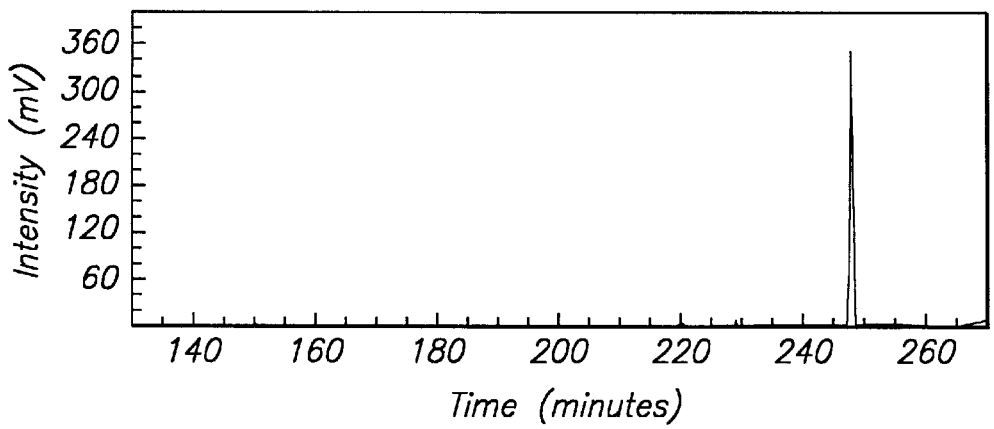
FIG. 12a shows, as a comparison, the chromatographic form of the 2,7-DMN used as feed in the hydroisomerization reaction described in Example 18.
Figure 12B:
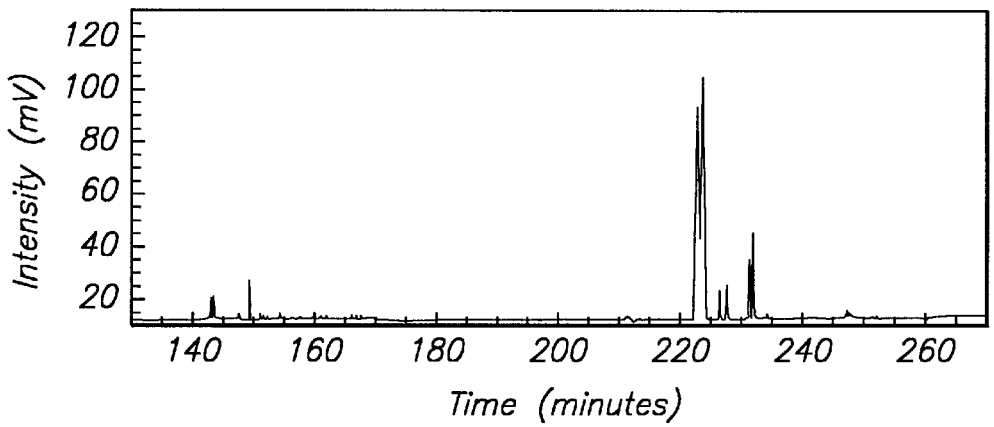
FIG. 12b shows in chromatographic form the hydroisomerization product of 2,7-DMN used as feed in the hydrogenation run described in Example 18.
Figure 12C:
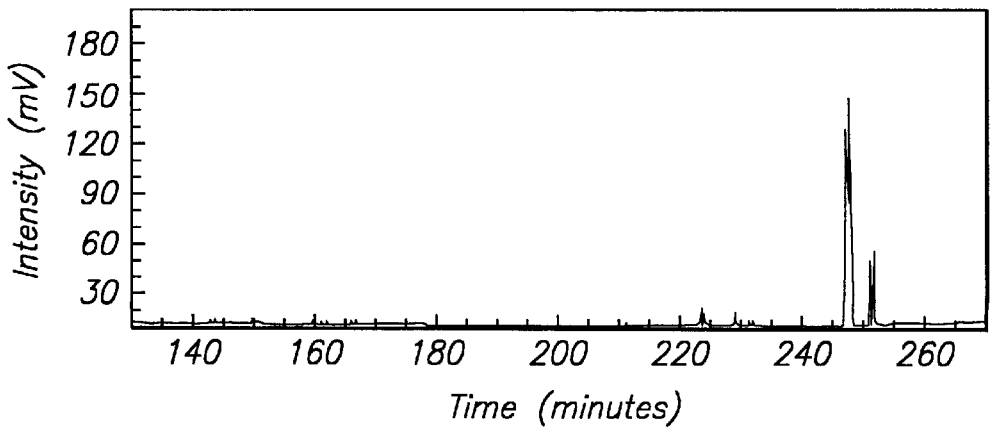
FIG. 12c shows the results of the dehydrogenation in chromatographic form.
Figure 12D:
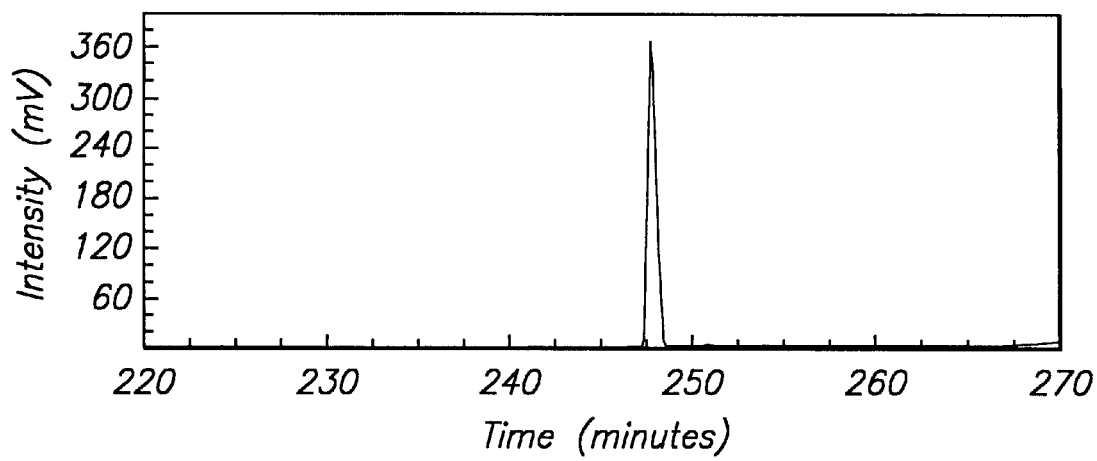
FIG. 12d shows, as a comparison to FIG. 12e, an expanded scale view of the chromatogram of the 2,7-DMN feed for the hydroisomerization described in Example 18.
Figure 12E:
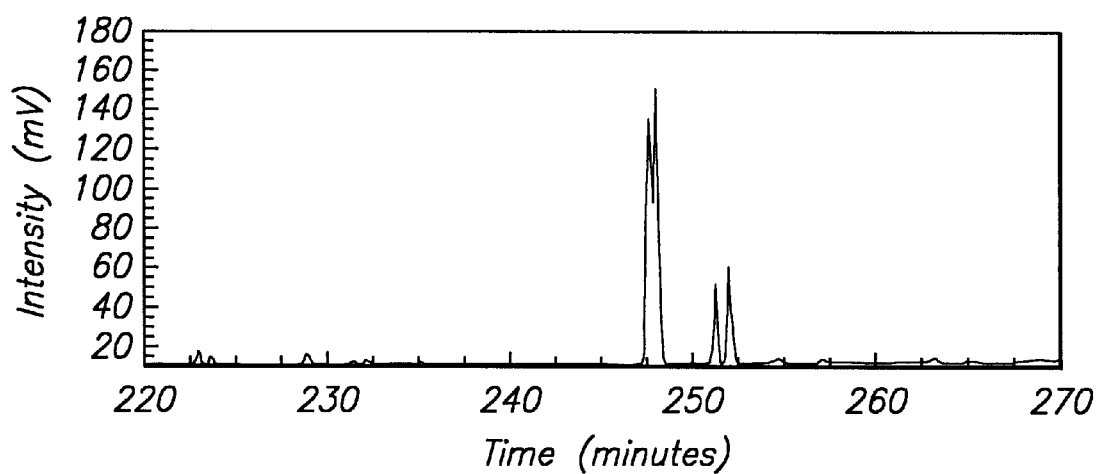
FIG. 12e shows in an expanded scale chromatographic form the product of the dehydrogenation reaction described in Example 18.

In Example 8, a hydrocarbon feed of 5:1 (wt:wt) o-xylene: 2,7-dimethylnaphthalene was hydroisomerized in a reactor with a Pd/Boron/Al/Beta catalyst (0.5 g) containing 500 ppm aluminum at 475° F. and 200 psig. The hydroisomerization products including the solvent o-xylene were collected and then dehydrogenated by being subjected as feed to PtS/Na-ZSM-5 in a reactor at 850° F., 100 psig, 0.5 ml/hr feed, 23 ml/min $H_2$ and 0.5 g catalyst. The feed for the dehydrogenation reaction (hydroisomerization products of 2,7-DMN) is shown in chromatographic form in FIG. 12b in comparison to 2,7-DMN (used as feed for the hydroisomerization in Example 8) in FIG. 12a. The result of the dehydrogenation is shown in chromatographic form in FIG. 12c. The results (significant peaks of 2,7- and 2,6-DMN and lesser peaks of 1,7- and 1,6-DMN) are shown on an expanded scale in FIG. 12e in comparison to 2,7-DMN (used as feed for the hydroisomerization in Example 8) in FIG. 12d. The compositions of the feed for the dehydrogenation reaction (hydroisomerization products of 2,7 DMN in Example 8) and its dehydrogenation product are shown in weight % in Table XVIII. The detailed GC peak identification is demonstrated in FIGS. 1a, 1b, 2a, 2b, 3a, 3b, 4a, 4b, 5a, 5b, 10a and 10b.

TABLE XVIII

|  | 2,7-DMN (used as feed for hydro-isomerization) | Feed for dehydrogenation (made from 2,7-DMN hydro-isomerization) | Product of de-hydrogenation |
| --- | --- | --- | --- |
| DMN's (total) | 100 | 2.1 | 94.2 |
| 2,7-DMN | 100 | 0.9 | 50.1 |
| 2,6-DMN | 0 | 0.6 | 27.5 |
| 1,7-DMN | 0 | 0.2 | 7.3 |
| 1,6-DMN | 0 | 0.2 | 9.1 |
| 1,5-DMN | 0 | 0.1 | 0.2 |
| other DMN's | 0 | 0.1 | 0 |
| DMD's + other $C12$'s | 0 | 8.7 | 1.7 |
| DMT's (total) | 0 | 89.2 | 4.1 |
| 1,5-DMT | 0 | 0.1 | 0 |
| 1,6-DMT | 0 | 2.4 | 0.1 |
| 2,5-DMT | 0 | 6.2 | 0.2 |
| 1,7-DMT | 0 | 2.4 | 0.1 |
| 2,8-DMT | 0 | 4.5 | 0.2 |
| 2,7-DMT | 0 | 43.7 | 1.7 |
| 2,6-DMT | 0 | 29.2 | 1.0 |
| 1,4-DMT | 0 | 0 | 0 |
| Other DMT's | 0 | 0.7 | 0.8 |
| MN's | 0 | 0 | 0 |

Example 19

Hydroisomerization/dehydrogenation of 2,7-DMN with PdS/Y and PtS/Na-ZSM-5

Figure 13A:
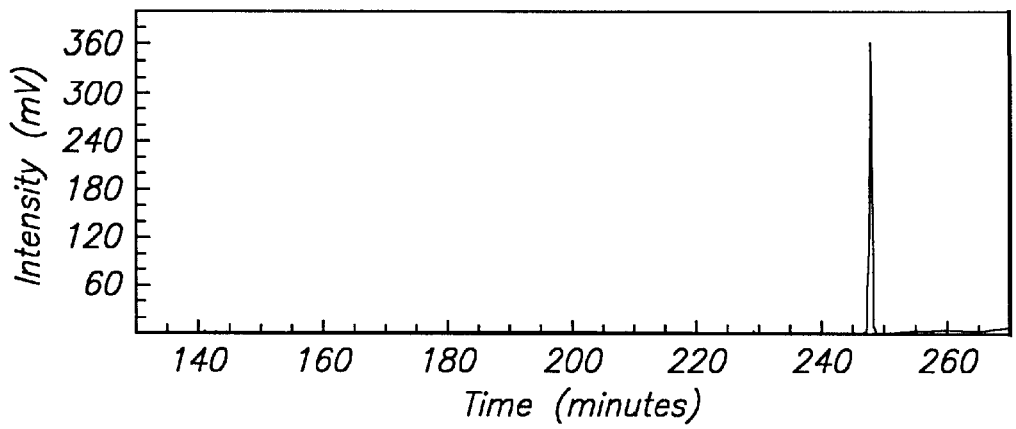
FIG. 13a shows, as a comparison, the chromatographic form of the 2,7-DMN used as feed in the hydroisomerization reaction described in Example 19.
Figure 13B:
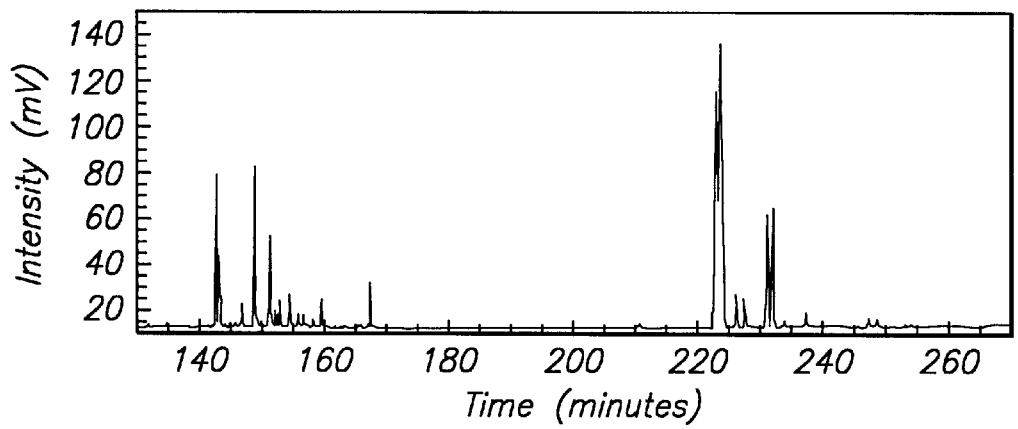
FIG. 13b shows in chromatographic form the hydroisomerization product of 2,7-DMN used as feed in the hydrogenation run described in Example 19.
Figure 13C:
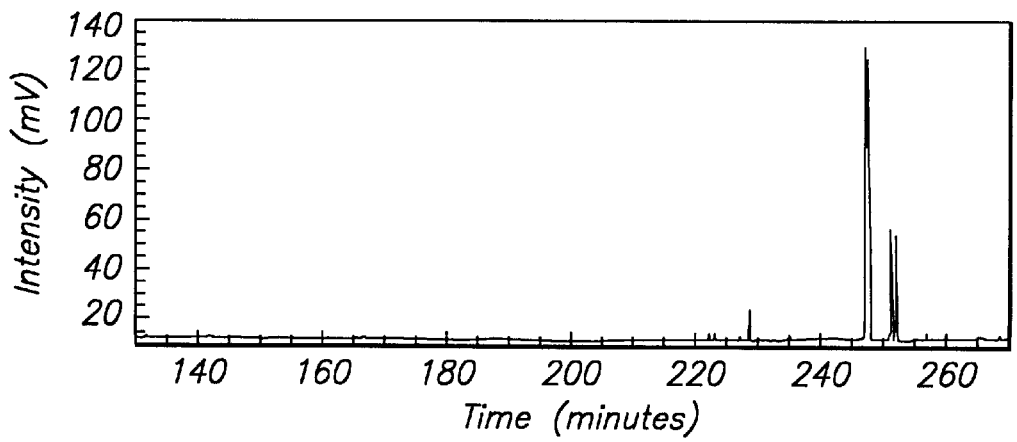
FIG. 13c shows the results of the dehydrogenation in chromatographic form.
Figure 13D:
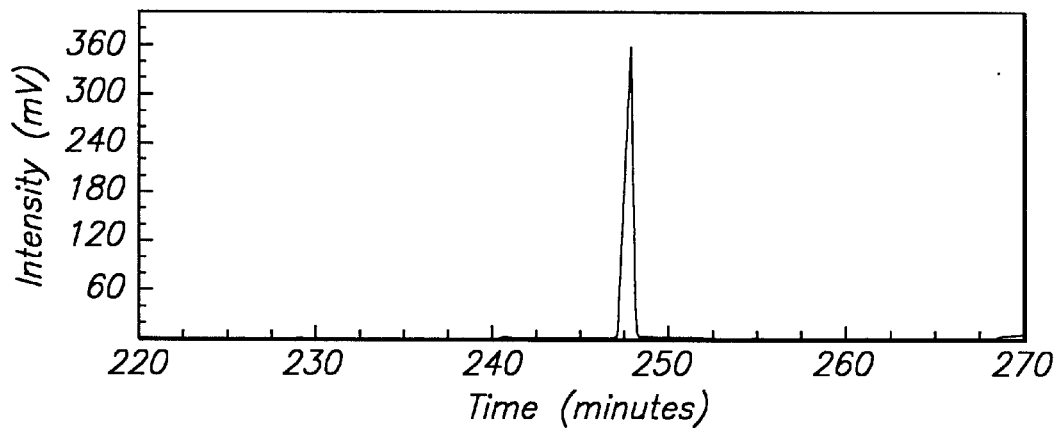
FIG. 13d shows, as a comparison to FIG. 13e, in an expanded scale chromatographic form the 2,7-DMN feed for the hydroisomerization run of Example 19.
Figure 13E:
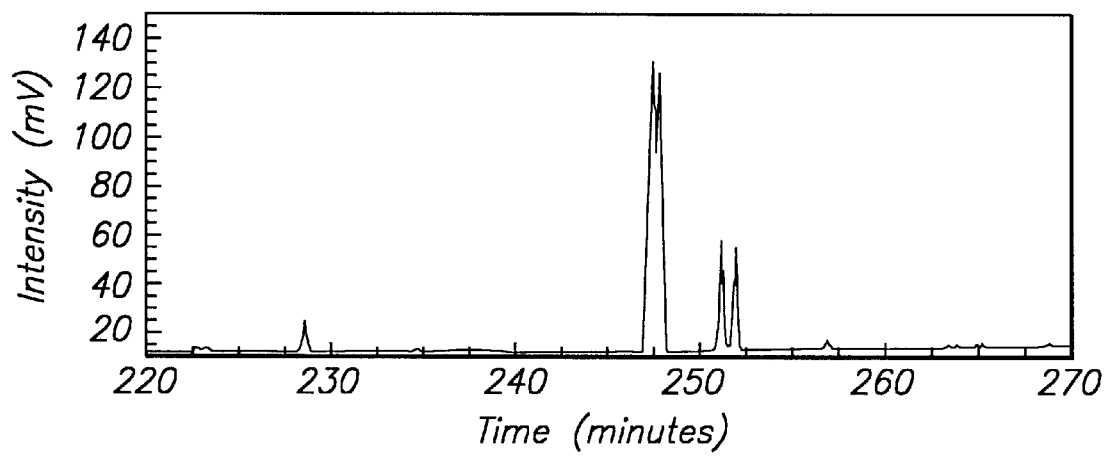
FIG. 13e shows in an expanded scale chromatographic form the product of the dehydrogenation reaction described in Example 19.

In Example 6, a hydrocarbon feed of 5:1 (wt:wt) o-xylene: 2,7-dimethylnaphthalene was hydroisomerized in a reactor with PdS/Y (0.5 g) catalyst at 400° F. and 500 psig. The hydroisomerization products including the solvent o-xylene were collected and then dehydrogenated by being subjected as feed to PtS/Na-ZSM-5 in a reactor at 850° F., 100 psig, 0.5 ml/hr feed, 23 ml/min $H_2$ and 0.5 g catalyst. The feed (hydroisomerization products of 2,7-DMN) is shown in chromatographic form in FIG. 13b in comparison to 2,7-DMN (used as feed for hydroisomerization in Example 6) in FIG. 13a. The result of the dehydrogenation is shown in chromatographic form in FIG. 13c. The results (significant peaks of 2,7- and 2,6-DMN and lesser peaks of 1,7- and 1,6-DMN) are shown on an expanded scale in FIG. 13e in comparison to 2,7-DMN (used as feed for hydroisomerization in Example 6) in FIG. 13d. The compositions of the feed (hydroisomerization products of 2,7-DMN in Example 6) and its dehydrogenation product are shown in weight % in Table XIX. The detailed GC peak identification is demonstrated in FIGS. 1a, 1b, 2a, 2b, 3a, 3b, 4a, 4b, 5a, 5b, 10a and 10b. The dehydrogenation catalyst was stable under these condition for at least 9 days.

TABLE XIX

| | 2,7-DMN (used as feed for hydro-isomerization) | Feed for dehydrogenation (made from 2,7-DMN hydro-isomerization) | Product of de-hydrogenation |
|---|---|---|---|
| DMN's (total) | 100 | 0.3 | 94.8 |
| 2,7-DMN | 100 | 0.1 | 52.7 |
| 2,6-DMN | 0 | 0.1 | 22.3 |
| 1,7-DMN | 0 | 0.1 | 9.7 |
| 1,6-DMN | 0 | 0 | 8.9 |
| 1,5-DMN | 0 | 0 | 0.9 |
| Other DMN's | 0 | 0 | 0.3 |
| DMD's + other C12's | 0 | 31.1 | 1.0 |
| DMT's(total) | 0 | 68.6 | 1.6 |
| 1,5-DMT | 0 | 0.3 | 0 |
| 1,6-DMT | 0 | 1.3 | 0.1 |
| 2,5-DMT | 0 | 6.0 | 0.1 |
| 1,7-DMT | 0 | 1.5 | 0.1 |
| 2,8-DMT | 0 | 5.9 | 0.1 |
| 2,7-DMT | 0 | 33.4 | 0.4 |
| 2,6-DMT | 0 | 20.1 | 0.3 |
| 1,4-DMT | 0 | 0 | 0 |
| Other DMT's | 0 | 0.1 | 0.5 |
| MN's | 0 | 0 | 2.6 |

Example 20

Hydroisomerization/dehydrogenation of 2,7-DMN with PdS/Y and PtS/Re/Al$_2$O$_3$

Figure 14A:
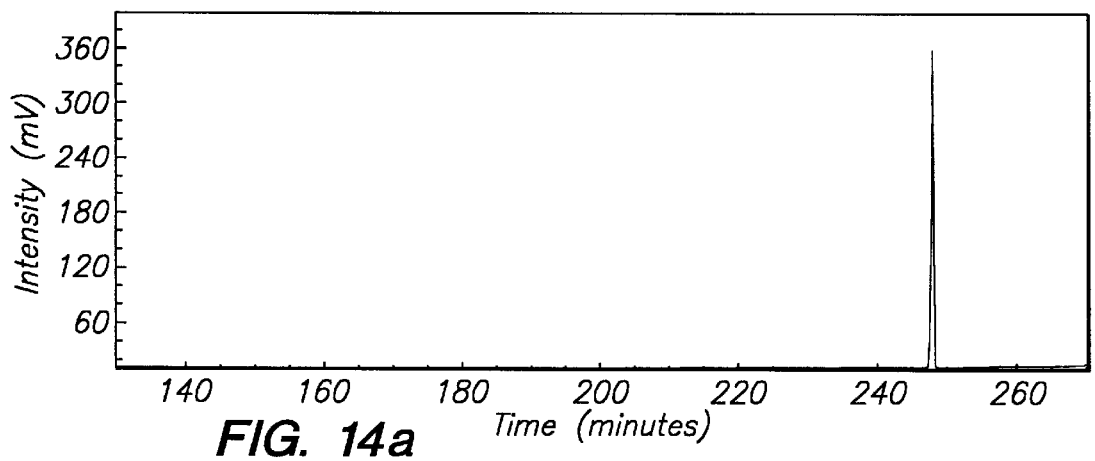
FIG. 14a shows in chromatographic form the 2,7-DMN feed used for the hydroisomerization run described in Example 20.
Figure 14B:
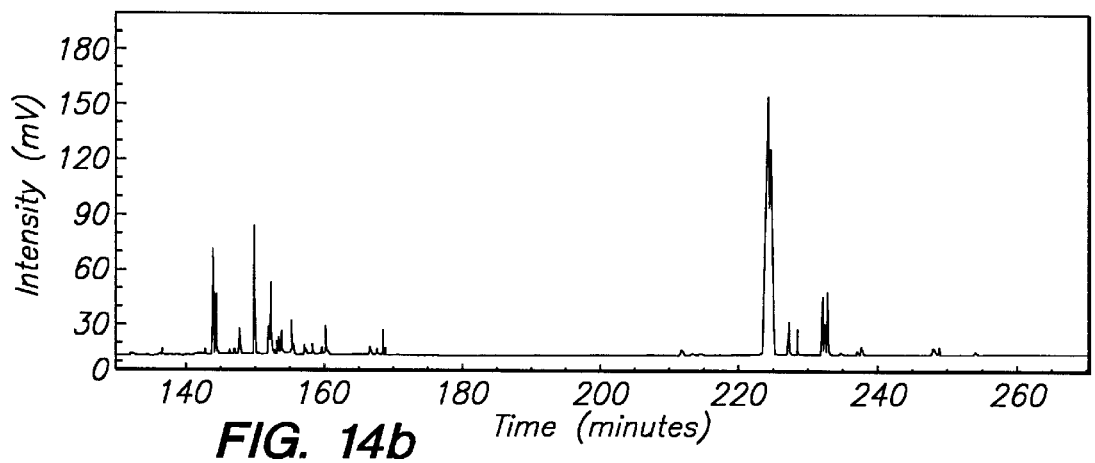
FIG. 14b shows in chromatographic form the feed for the dehydrogenation reaction described in Example 20. The result of the dehydrogenation is shown in chromatographic form in FIG. 14c.
Figure 14C:
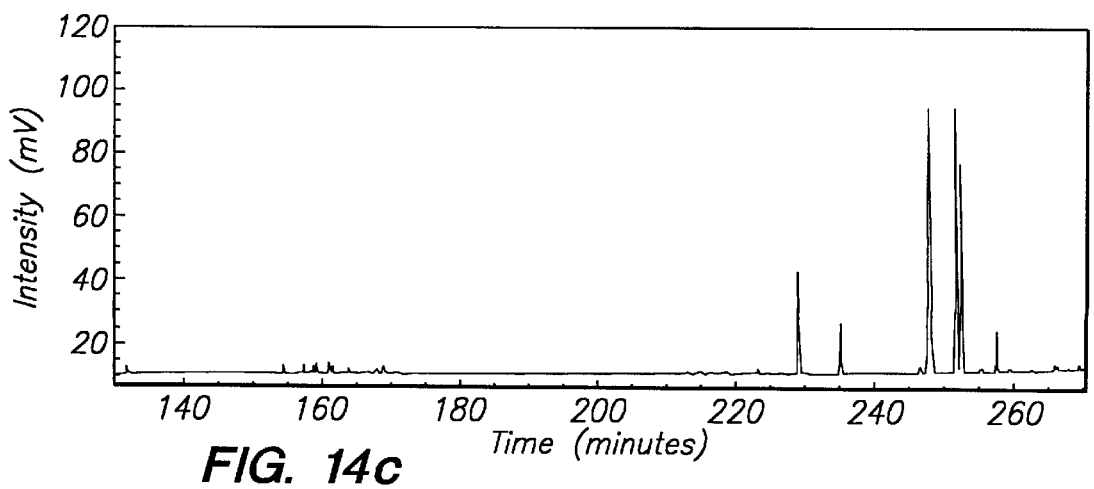
FIG. 14e shows in an expanded scale chromatographic form the product of the dehydrogenation reaction described in Example 20.
FIG. 14d shows, as a comparison to FIG. 14e, an expanded scale view of the chromatogram of the 2,7-DMN feed for the hydroisomerization run of Example 20.
Figure 14D:
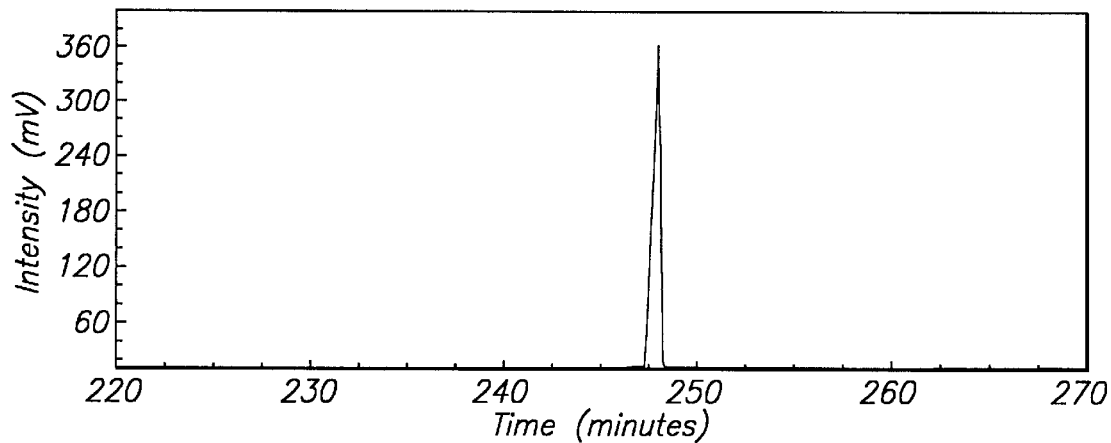
Figure 14E:
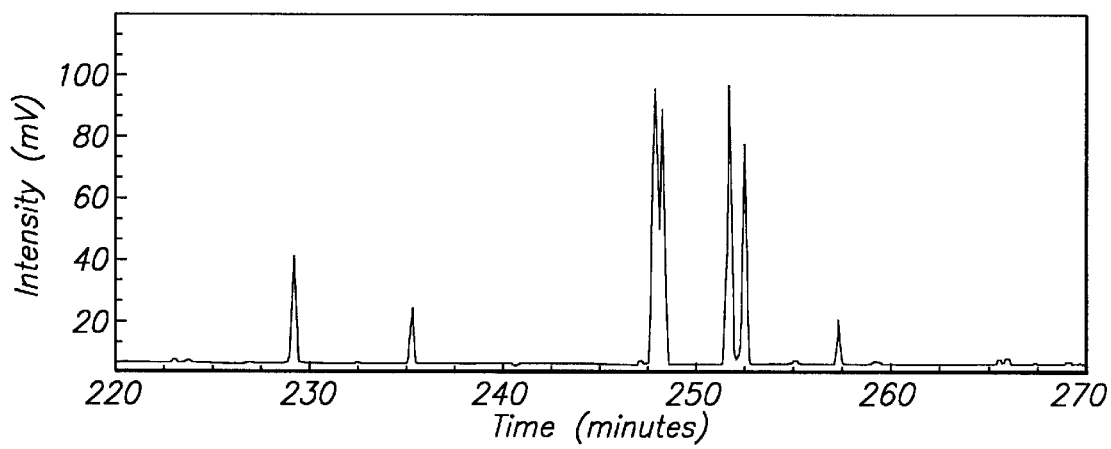

A hydrocarbon feed of 5:1 (wt:wt) o-xylene:2,7-dimethylnaphthalene was hydroisomerized in a reactor with PdS/Y catalyst at 350–475° F., 200 psig, 1.0 ml/hr feed, 40 ml/min H$_2$ and 0.5 g catalyst. The hydroisomerization product including the solvent o-xylene was collected and then dehydrogenated by being fed to a sulfided Pt/Re/Al$_2$O$_3$ catalyst (0.3 wt. % Pt, 0.3 wt. % Re, 1.1 wt. % Cl on Al$_2$O$_3$) in a reactor at 850° F., 100 psig, 0.3 ml/hr feed, 23 ml/min H$_2$ and 0.5 g catalyst. The 2,7-DMN feed used for hydroisomerization is shown in FIG. 14a. The feed for the dehydrogenation (which is the hydroisomerization products of 2,7-DMN) is shown in chromatographic form in FIG. 14b. The result of the dehydrogenation is shown in chromatographic form in FIG. 14c. The results (significant peaks of 2,7-, 2,6-, 1,7- and 1,6-DMN and lesser peak of 1,5-DMN) are shown on an expanded scale in FIG. 14e in comparison to 2,7-DMN (used as feed for hydroisomerization) in FIG. 14d. It appears that due to the acidic properties of Pt/Re/Al$_2$O$_3$ catalyst a significant amount of methylnaphthalenes were produced as by-products in the dehydrogenation step when Pt/Re/Al$_2$O$_3$ was used as dehydrogenation catalyst. The compositions of the 2,7-DMN feed (for the hydroisomerization), the dehydrogenation feed (hydroisomerization products of 2,7-DMN) and the dehydrogenation product are shown in weight % in Table XX.

TABLE XX

| | 2,7-DMN (used as feed for hydro-isomerization) | Feed for dehydrogenation (made from 2,7-DMN hydro-isomerization) | Product of de-hydrogenation |
|---|---|---|---|
| DMN's (total) | 100 | 0.8 | 85.3 |
| 2,7-DMN | 100 | 0.4 | 27.5 |
| 2,6-DMN | 0 | 0.2 | 15.9 |

TABLE XX-continued

| | 2,7-DMN (used as feed for hydro-isomerization) | Feed for dehydrogenation (made from 2,7-DMN hydro-isomerization) | Product of de-hydrogenation |
|---|---|---|---|
| 1,7-DMN | 0 | 0.1 | 22.3 |
| 1,6-DMN | 0 | 0.1 | 16.4 |
| 1,5-DMN | 0 | 0 | 2.9 |
| Other DMN's | 0 | 0 | 0.3 |
| DMD's + other C12's | 0 | 32.5 | 2.7 |
| DMT's (total) | 0 | 66.7 | ~0 |
| 1,5-DMT | 0 | 0.2 | ~0 |
| 1,6-DMT | 0 | 1.4 | ~0 |
| 2,5-DMT | 0 | 3.4 | ~0 |
| 1,7-DMT | 0 | 1.9 | ~0 |
| 2,8-DMT | 0 | 3.5 | ~0 |
| 2,7-DMT | 0 | 42.7 | ~0 |
| 2,6-DMT | 0 | 13.5 | ~0 |
| 1,4-DMT | 0 | 0 | ~0 |
| Other DMT's | 0 | 0.1 | ~0 |
| 1-MN | 0 | 0 | 3.5 |
| 2-MN | 0 | 0 | 8.3 |
| TMN's | 0 | 0 | 0.2 |

Example 21

Hydrogenation/dehydrogenation of 1.5-DMN with PtS/B-SSZ-33 and PtS/Na-ZSM-5

Figure 15A:
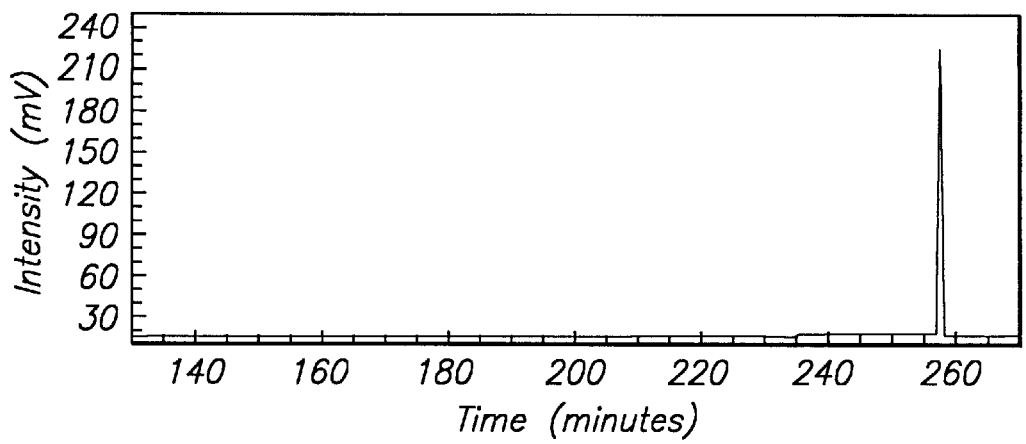
FIG. 15a shows, as a comparison to FIG. 15b, an expanded view of the chromatogram of the 1,5-DMN feed for the hydrogenation run described in Examples 1 and 21. The result of the dehydrogenation is shown in chromatographic form in FIG. 15c.
Figure 15B:
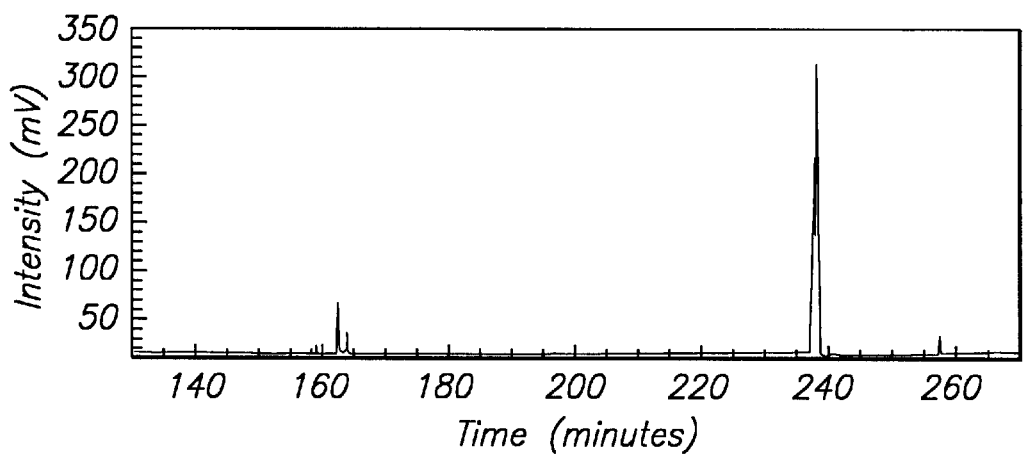
FIG. 15b shows in chromatographic form the product of the dehydrogenation reaction described in Example 21.
Figure 15C:
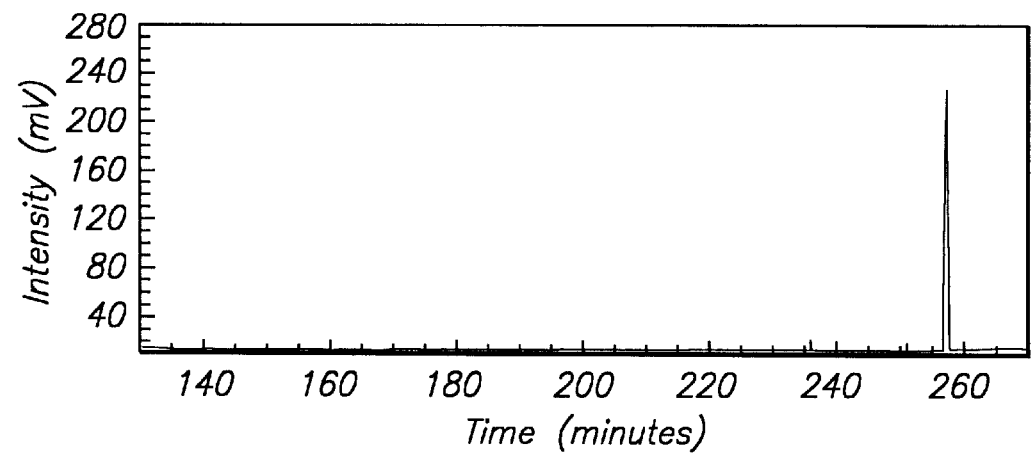

In Example 1, a hydrocarbon feed of 5:1 (wt:wt) o-xylene:1,5-dimethylnaphthalene was hydrogenated in a reactor with a PtS/Boron-SSZ-33 catalyst (0.5 g) at 400° F. and 200 psig. The hydrogenation products including the solvent o-xylene were collected and then dehydrogenated by being fed to PtS/Na-ZSM-5 in a reactor at 850° F., 100 psig, 0.5 ml/hr feed, 23 ml/min H$_2$ and 0.5 g catalyst. The feed (hydrogenation products of 1,5-DMN) is shown in chromatographic form in FIG. 15b in comparison to 1,5-DMN (used as feed for hydrogenation in Example 1) in FIG. 15a. The result of the dehydrogenation is shown in chromatographic form in FIG. 15c. As described in Example 1, in the hydrogenation step, 96% of 1,5-DMN was converted, yielding 88% 1,5-DMT and 8% DMD's and other C12's. No other DMT isomers were observed. In the dehydrogenation step of this example, the resulting dehydrogenation product has the following composition: ~0% DMD's and other C12's, 0.9% 1,5-DMT, 1.3% other DMT's, 96.5% 1,5-DMN, 1.3% 1,6/1,7-DMN. No MN's were detected. The detailed GC peak identification is demonstrated in FIGS. 1a, 1b, 2a, 2b, 3a, 3b, 4a, 4b, 5a, 5b, 10a and 10b. Since PtS/Na-ZSM-5 works for the "bulky" 1,5-isomers as demonstrated in this example, this catalyst apparently also works for the dehydrogenation of other DMN isomers.

Example 22

Hydroisomerization/dehydrogenation of 1,5-DMN with PdS/Y and PtS/Na- ZSM-5

Figure 16A:
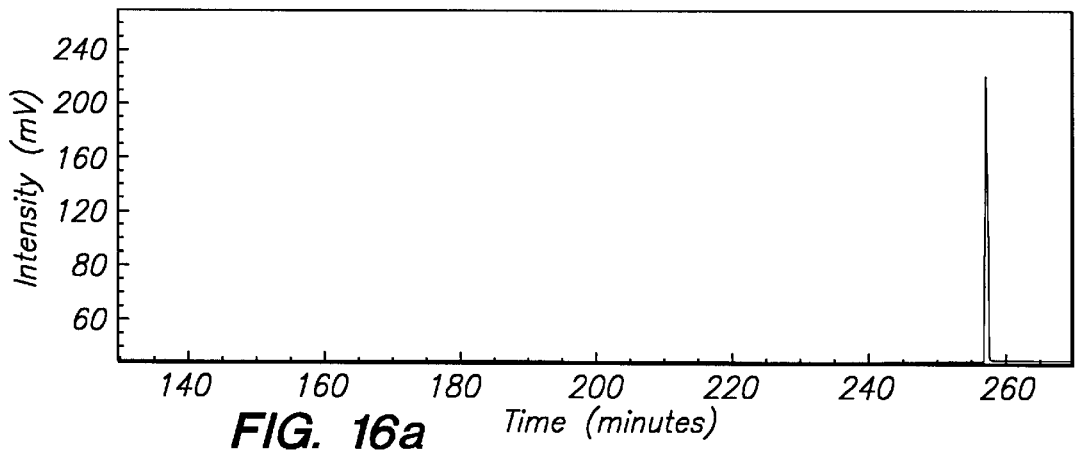
FIG. 16a shows in chromatographic form the 1,5-DMN feed used for the hydroisomerization run described in Example 22.
Figure 16B:
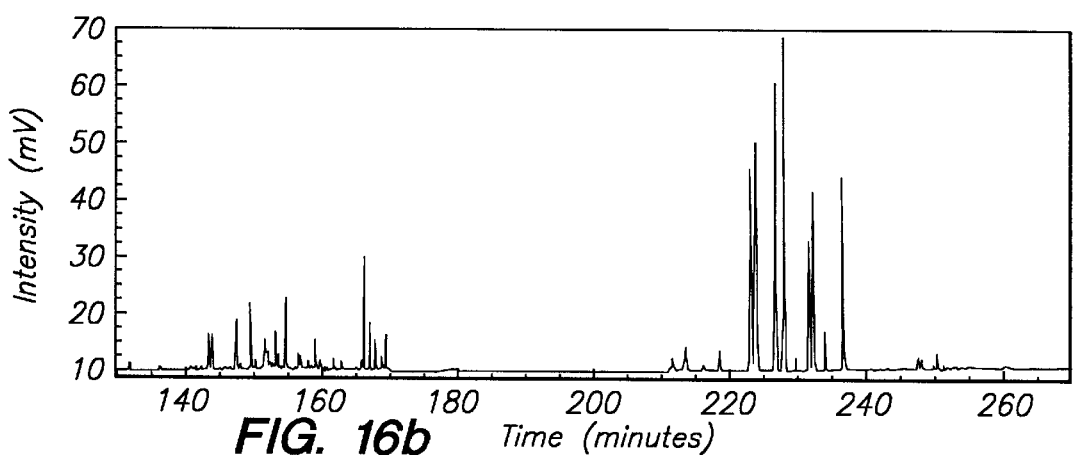
FIG. 16b shows in chromatographic form the feed for the dehydrogenation reaction described in Example 22. The result of the dehydrogenation is shown in chromatographic form in FIG. 16c.
Figure 16C:
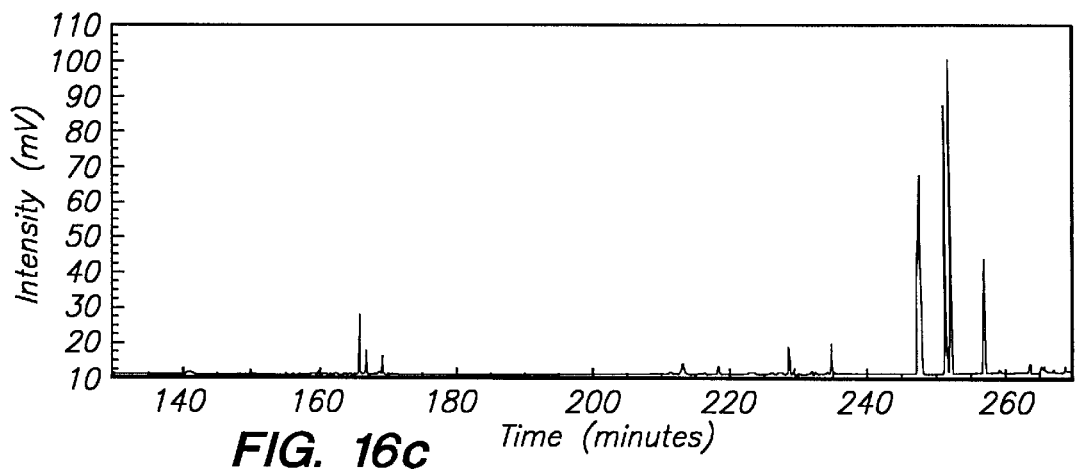
FIG. 16e shows in a closer scale chromatographic form the product of the dehydrogenation reaction described in Example 22.
FIG. 16d shows, as a comparison to FIG. 16e, a closer scale view of the chromatogram of the 1,5-DMN feed for the hydroisomerization run of Example 22.
Figure 16D:
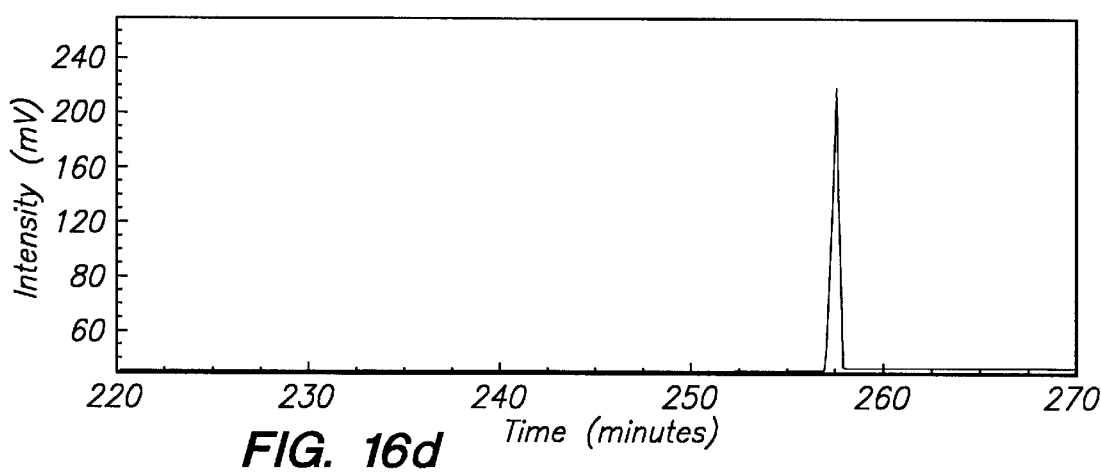
Figure 16E:
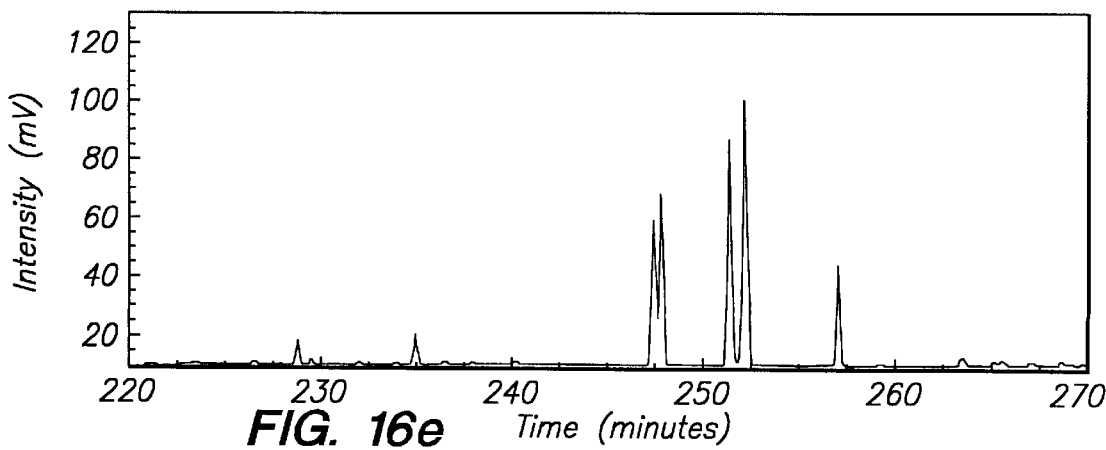

A hydrocarbon feed of 5:1 (wt:wt) o-xylene: 1,5-dimethylnaphthalene was hydroisomerized in a reactor with a PdS/Y catalyst at 440° F., 500 psig, 0.5 ml/hr feed, 40 ml/min H$_2$ and 0.5 g catalyst. The hydroisomerization products including the solvent o-xylene were collected and then dehydrogenated by being fed to a PtS/Na-ZSM-5 in a reactor at 850° F., 100 psig, 0.5 ml/hr feed, 23 ml/min H$_2$ and 0.5 g catalyst. The 1,5-DMN feed used for hydroisomerization is shown in FIG. 16a. The feed for the dehydrogenation (which is the hydroisomerization products of 1,5-DMN) is shown in chromatographic form in FIG. 16b. The result of the dehydrogenation is shown in chromatographic form in FIG. 16c. The results (significant peaks of 2,7-, 2,6-, 1,7- and 1,6-DMN and lesser peak of 1,5-DMN) are shown on an expanded scale in FIG. 16e in comparison to 1,5-DMN (used as feed for hydroisomerization) in FIG. 16d. The detailed GC peak identification is demonstrated in FIGS. 1a, 1b, 2a, 2b, 3a, 3b, 4a, 4b, 5a, 5b, 10a and 10b. The compositions of the 1,5-DMN feed (for the hydroisomerization), the dehydrogenation feed (hydroisomerization products of 1,5-DMN), and the dehydrogenation product are shown in weight % in Table XXII.

TABLE XXII

|  | 1,5-DMN (used as feed for hydro-isomerization) | Feed for dehydrogenation (made from 1,5-DMN hydro-isomerization) | Product of de-hydrogenation |
|---|---|---|---|
| DMN's (total) | 100 | 2.6 | 81.7 |
| 2,7-DMN | 0 | 0.7 | 12.9 |
| 2,6-DMN | 0 | 0.6 | 13.3 |
| 1,7-DMN | 0 | 0.3 | 20.9 |
| 1,6-DMN | 0 | 0.2 | 26.3 |
| 1,5-DMN | 100 | 0.1 | 7.9 |
| Other DMN's | 0 | 0.7 | 0.4 |
| DMD's + other C12's | 0 | 26.2 | 7.5 |
| DMT's (total) | 0 | 70.8 | 5.6 |
| 1,5-DMT | 0 | 6.5 | 0.2 |
| 1,6-DMT | 0 | 14.3 | 0.1 |
| 2,5-DMT | 0 | 6.7 | 0.1 |
| 1,7-DMT | 0 | 12.7 | 0.2 |
| 2,8-DMT | 0 | 4.7 | 0.1 |
| 2,7-DMT | 0 | 9.7 | 0.1 |
| 2,6-DMT | 0 | 10.7 | 0.2 |
| 1,4-DMT | 0 | 0 | 0 |
| Other DMT's | 0 | 5.5 | 4.6 |
| 1-MN | 0 | 0 | 2.2 |
| 2-MN | 0 | 0 | 2.0 |
| TMN's | 0 | 0.4 | 1.0 |

Example 23

Hydroisomerization/dehydrogenation of 1,6-DMN with PdS/Y and PtS/Na-ZSM-5

Figure 17A:
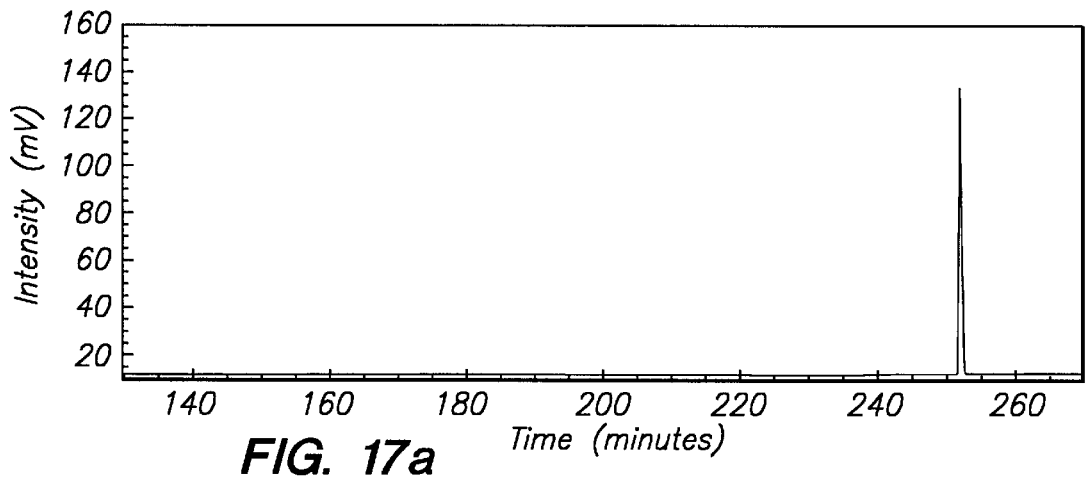
FIG. 17a shows in chromatographic form the 1,6-DMN feed used for the hydroisomerization run described in Example 23.
Figure 17B:
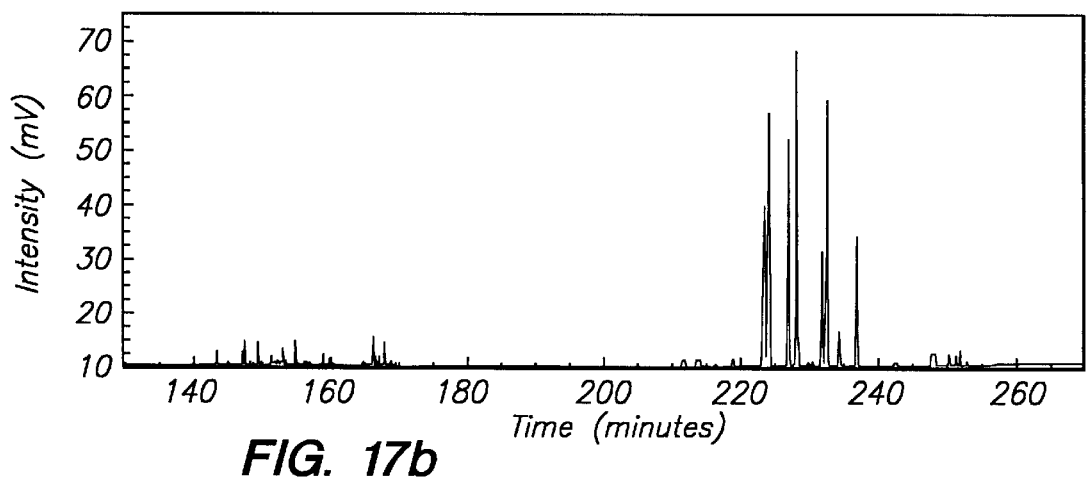
FIG. 17b shows in chromatographic form the feed for the dehydrogenation reaction described in Example 23. The result of the dehydrogenation is shown in chromatographic form in FIG. 17c.
Figure 17C:
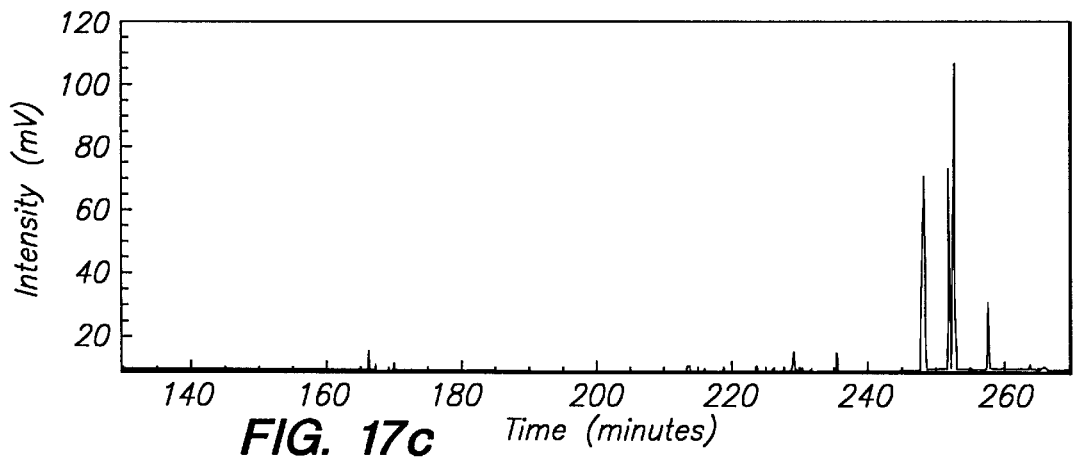
FIG. 17e shows in a closer scale chromatographic form the product of the dehydrogenation reaction described in Example 23.
FIG. 17d shows, as a comparison to FIG. 17e, a closer scale view of the chromatogram of the 1,6-DMN feed for the hydroisomerization run of Example 23.
Figure 17D:
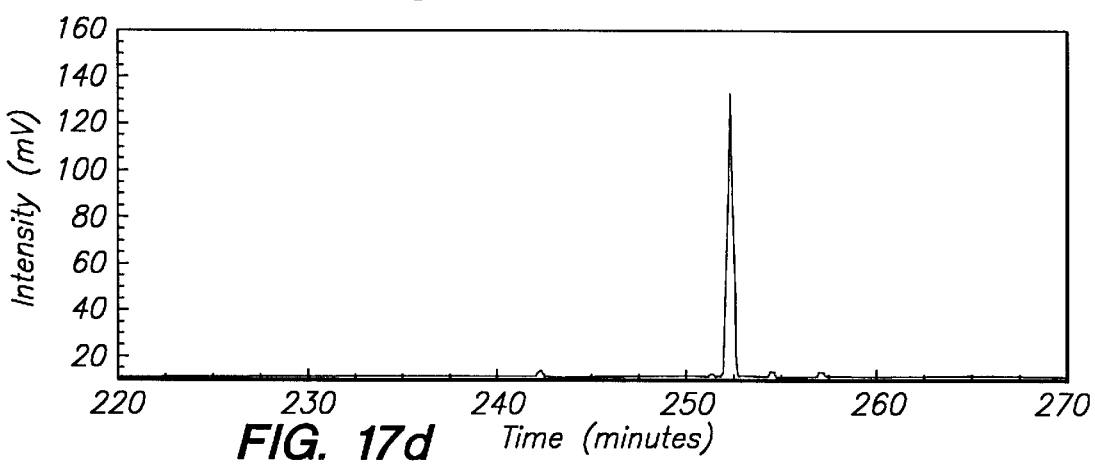
Figure 17E:
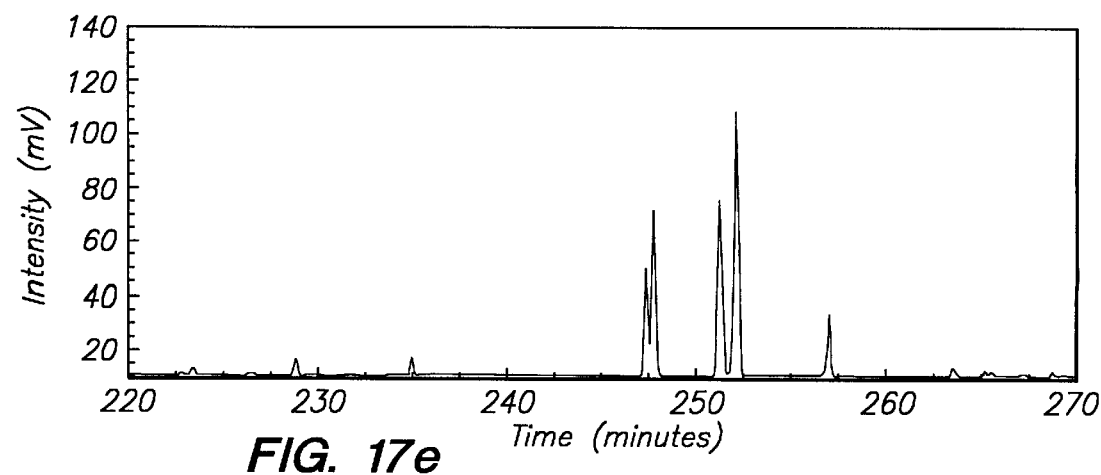

A hydrocarbon feed of 5:1 (wt:wt) o-xylene: 1,6-dimethylnaphthalene was hydroisomerized in a reactor with PdS/Y catalyst at 440° F., 500 psig, 0.5 ml/hr feed, 40 ml/min H$_2$ and 0.5 g catalyst. The hydroisomerization products including the solvent o-xylene were collected and then dehydrogenated by being subjected as feed to a PtS/Na-ZSM-5 in a reactor at 850° F., 100 psig, 0.5 ml/hr feed, 23 ml/min H$_2$ and 0.5 g catalyst. The 1,6-DMN feed used for hydroisomerization is shown in FIG. 17a. The feed for the dehydrogenation (which is the hydroisomerization products of 1,6-DMN) is shown in chromatographic form in FIG. 17b. The result of the dehydrogenation is shown in chromatographic form in FIG. 17c. The results (significant peaks of 2,7-, 2,6-, 1,7- and 1,6-DMN and lesser peak of 1,5-DMN) are shown on an expanded scale in FIG. 17e in comparison to 1,6-DMN (used as feed for hydroisomerization) in FIG. 17d. The detailed GC peak identification is demonstrated in FIGS. 1a, 1b, 2a, 2b, 3a, 3b, 4a, 4b, 5a, 5b, 10a and 10b. The compositions of the 1,6-DMN feed (for the hydroisomerization), the dehydrogenation feed (hydroisomerization products of 1,6-DMN) and the dehydrogenation product are shown in weight % in Table XXIII.

TABLE XXIII

|  | 1,6-DMN (used as feed for hydro-isomerization) | Feed for dehydrogenation (made from 1,6-DMN hydro-isomerization) | Product of de-hydrogenation |
|---|---|---|---|
| DMN's (total) | 100 | 2.2 | 86.8 |
| 2,7-DMN | 0 | 0.5 | 11.0 |
| 2,6-DMN | 0 | 0.3 | 16.9 |
| 1,7-DMN | 0.7 | 0.3 | 18.7 |
| 1,6-DMN | 98.0 | 0.5 | 33.8 |
| 1,5-DMN | 0.7 | 0.1 | 5.8 |
| Other DMN's | 0.6 | 0.5 | 0.6 |
| DMD's + other C12's | 0 | 10.4 | 2.7 |
| DMT's (total) | 0 | 86.4 | 4.7 |
| 1,5-DMT | 0 | 5.6 | 0.1 |
| 1,6-DMT | 0 | 17.8 | 0.1 |
| 2,5-DMT | 0 | 13.9 | 0.1 |
| 1,7-DMT | 0 | 11.9 | 0.1 |
| 2,8-DMT | 0 | 5.7 | 0.1 |
| 2,7-DMT | 0 | 10.0 | 0.1 |
| 2,6-DMT | 0 | 16.6 | 0.6 |
| 1,4-DMT | 0 | 0 | 0 |
| Other DMT's | 0 | 4.9 | 3.5 |
| 1-MN | 0 | 0 | 1.7 |
| 2-MN | 0 | 0 | 1.7 |
| TMN's | 0 | 1.0 | 2.4 |

Example 24

Hydroisomerization/dehydrogenation of 1,7-DMN with PdS/Y and PtS/Na-ZSM-5

Figure 18A:
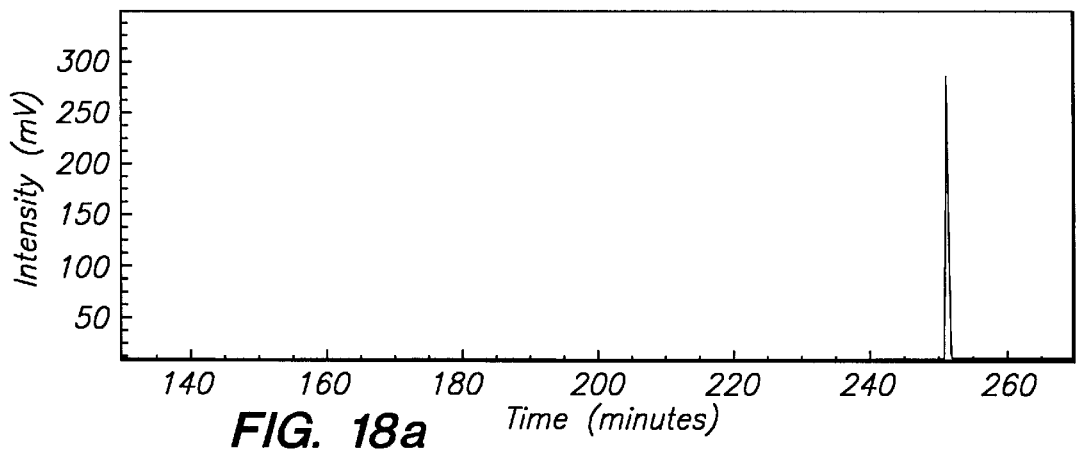
FIG. 18a shows in chromatographic form the 1,7-DMN feed used for the hydroisomerization run described in Example 24.
Figure 18B:
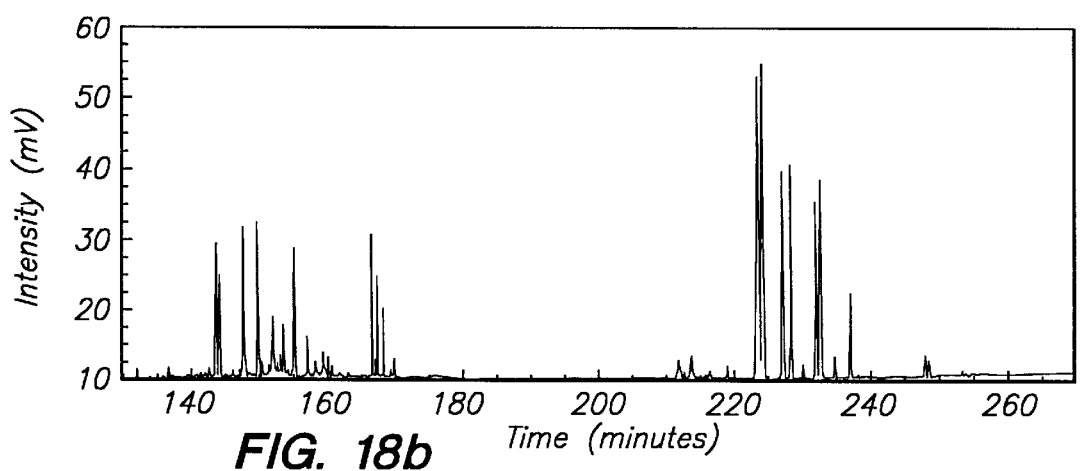
FIG. 18b shows in chromatographic form the feed for the dehydrogenation reaction described in Example 24. The result of the dehydrogenation is shown in chromatographic form in FIG. 18c.
Figure 18C:
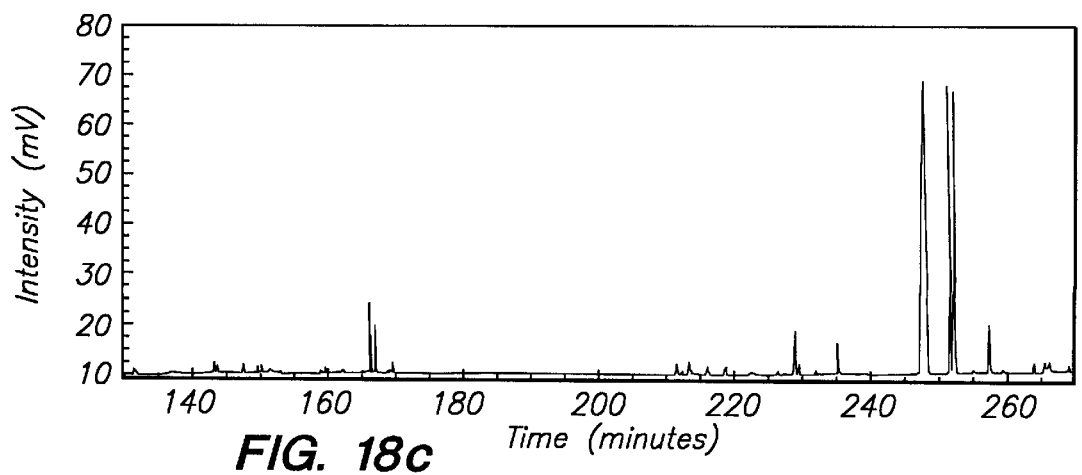
FIG. 18e shows in a closer scale chromatographic form the product of the dehydrogenation reaction described in Example 24.
FIG. 18d shows, as a comparison to FIG. 18e, a closer scale view of the chromatogram of the 1,7-DMN feed for the hydroisomerization run of Example 24.
Figure 18D:
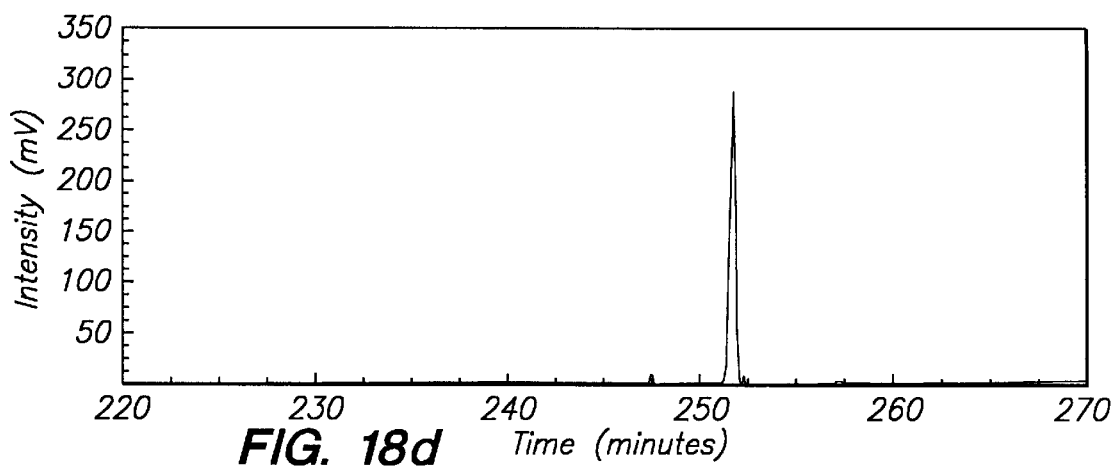
Figure 18E:
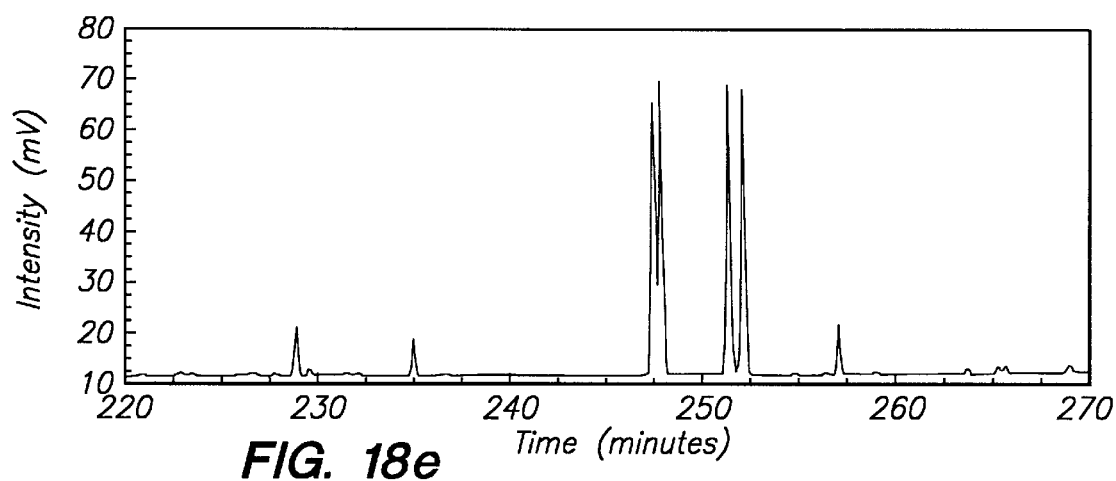

A hydrocarbon feed of 5:1 (wt:wt) o-xylene:1,7-dimethylnaphthalene was hydroisomerized in a reactor with PdS/Y catalyst at 440° F., 500 psig, 0.5 ml/hr feed, 40 ml/min H$_2$ and 0.5 g catalyst. The hydroisomerization products including the solvent o-xylene were collected and then dehydrogenated by being fed to PtS/Na-ZSM-5 in a reactor at 850° F., 100 psig, 1.0 ml/hr feed, 23 ml/min H$_2$ and 0.5 g catalyst. The 1,7-DMN feed used for hydroisomerization is shown in FIG. 18a. The feed for the dehydrogenation (which is the hydroisomerization products of 1,7-DMN) is shown in chromatographic form in FIG. 18b. The result of the dehydrogenation is shown in chromatographic form in FIG. 18c. The results (significant peaks of 2,7-, 2,6-, 1,7- and 1,6-DMN and lesser peak of 1,5-DMN) are shown on an expanded scale in FIG. 18e in comparison to 1,7-DMN (used as feed for hydroisomerization) in FIG. 18d. The detailed GC peak identification is demonstrated in FIGS. 1a, 1b, 2a, 2b, 3a, 3b, 4a, 4b, 5a, 5b, 10a and 10b. The compositions of the 1,7-DMN feed (for the hydroisomerization), the dehydrogenation feed (hydroisomerization products of 1,7-DMN), and the dehydrogenation product are shown in weight % in Table XXIV.

TABLE XXIV

|  | 1,7-DMN (used as feed for hydro-isomerization) | Feed for dehydrogenation (made from 1,7-DMN hydro-isomerization) | Product of de-hydrogenation |
|---|---|---|---|
| DMN's (total) | 100 | 2.4 | 78.4 |
| 2,7-DMN | 0 | 0.5 | 20.2 |
| 2,6-DMN | 0 | 0.4 | 17.0 |

TABLE XXIV-continued

|  | 1,7-DMN (used as feed for hydro-isomerization) | Feed for dehydrogenation (made from 1,7-DMN hydro-isomerization) | Product of de-hydrogenation |
|---|---|---|---|
| 1,7-DMN | 100 | 0.2 | 19.4 |
| 1,6-DMN | 0 | 0.2 | 18.2 |
| 1,5-DMN | 0 | 0.1 | 3.0 |
| Other DMN's | 0 | 1.0 | 0.6 |
| DMD's + other C12's | 0 | 40.4 | 10.0 |
| DMT's (total) | 0 | 57.2 | 5.6 |
| 1,5-DMT | 0 | 2.3 | 0.2 |
| 1,6-DMT | 0 | 7.1 | 0.1 |
| 2,5-DMT | 0 | 5.7 | 0.2 |
| 1,7-DMT | 0 | 6.9 | 0.2 |
| 2,8-DMT | 0 | 5.5 | 0.2 |
| 2,7-DMT | 0 | 12.4 | 0.2 |
| 2,6-DMT | 0 | 12.6 | 0.3 |
| 1,4-DMT | 0 | 0 | 0 |
| Other DMT's | 0 | 4.7 | 4.2 |
| 1-MN | 0 | 0 | 1.9 |
| 2-MN | 0 | 0 | 2.8 |
| TMN's | 0 | 0 | 1.3 |

Example 25

Hydroisomerization/dehydrogenation of a DMN mixture with PdS/Y and PtS/Na-ZSM-5

Figure 19A:
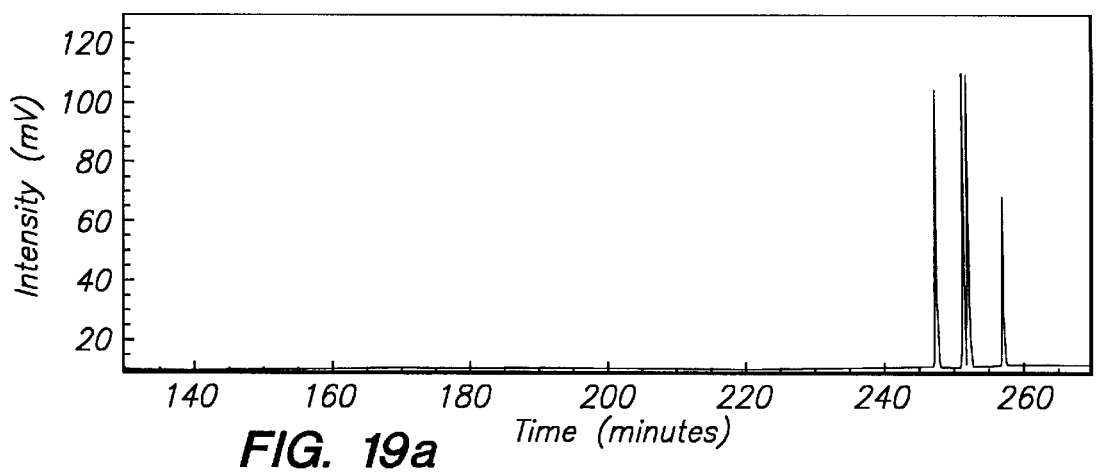
FIG. 19a shows in chromatographic form the DMN mixture feed used for the hydroisomerization run described in Example 25.
Figure 19B:
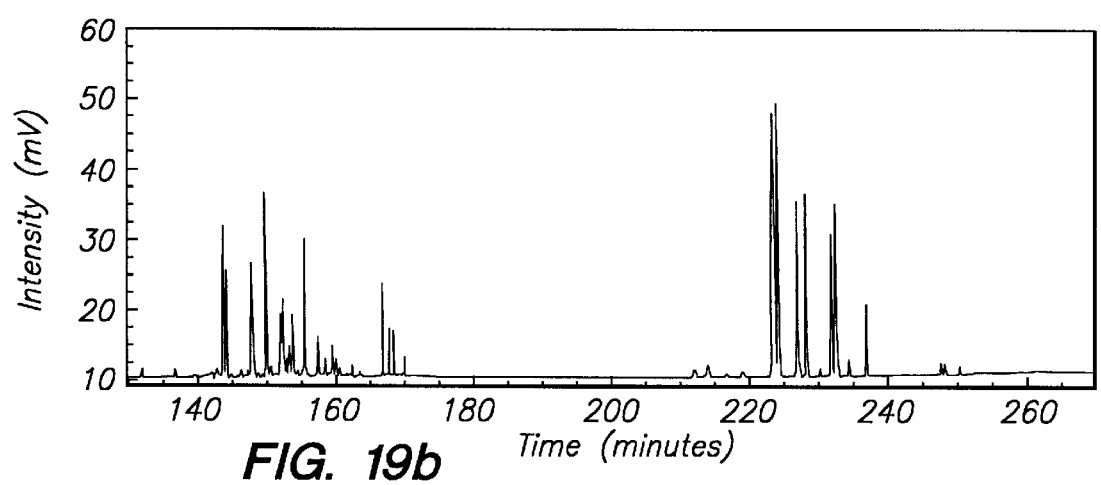
FIG. 19b shows in chromatographic form the feed for the dehydrogenation reaction described in Example 25. The result of the dehydrogenation is shown in chromatographic form in FIG. 19c.
Figure 19C:
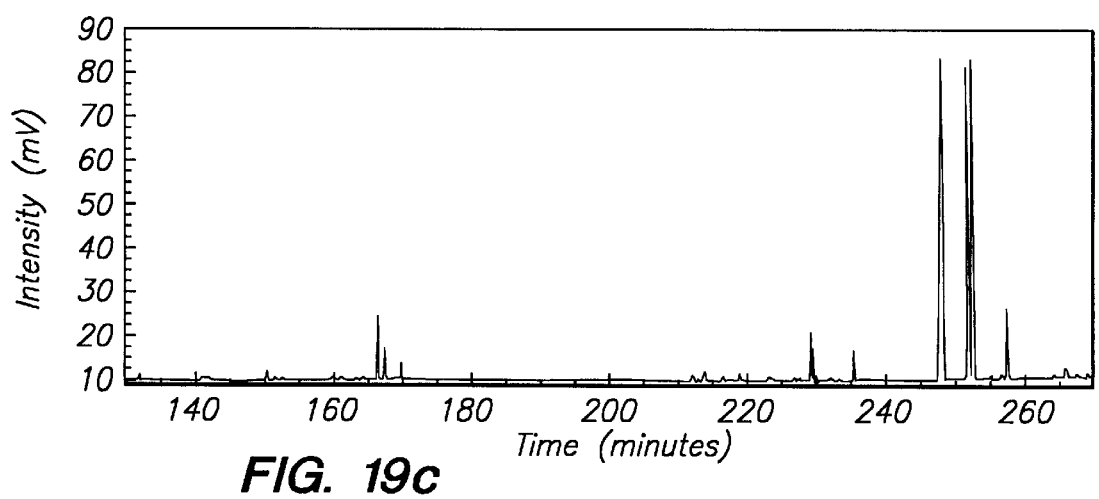
FIG. 19e shows in a closer scale chromatographic form the product of the dehydrogenation reaction described in Example 25.
FIG. 19d shows, as a comparison to FIG. 19e, a closer scale view of the chromatogram of the DMN mixture feed for the hydroisomerization run of Example 25.
Figure 19D:
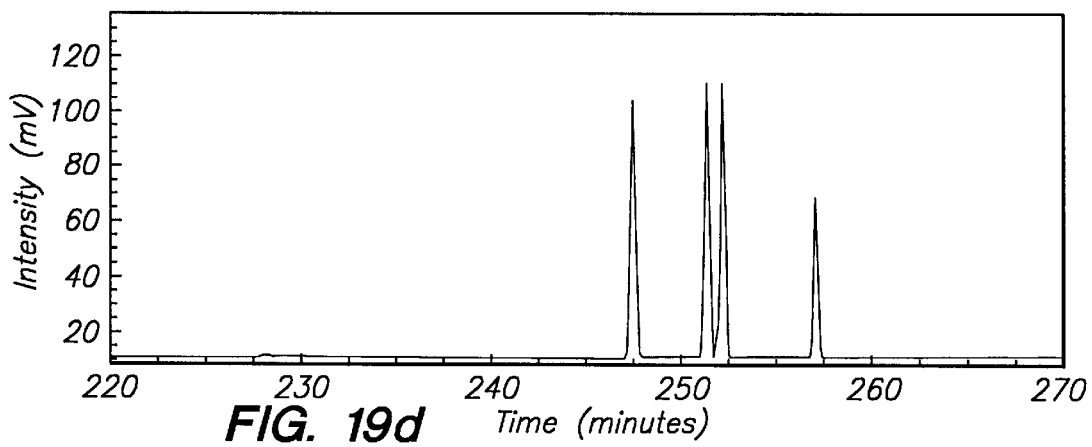
Figure 19E:
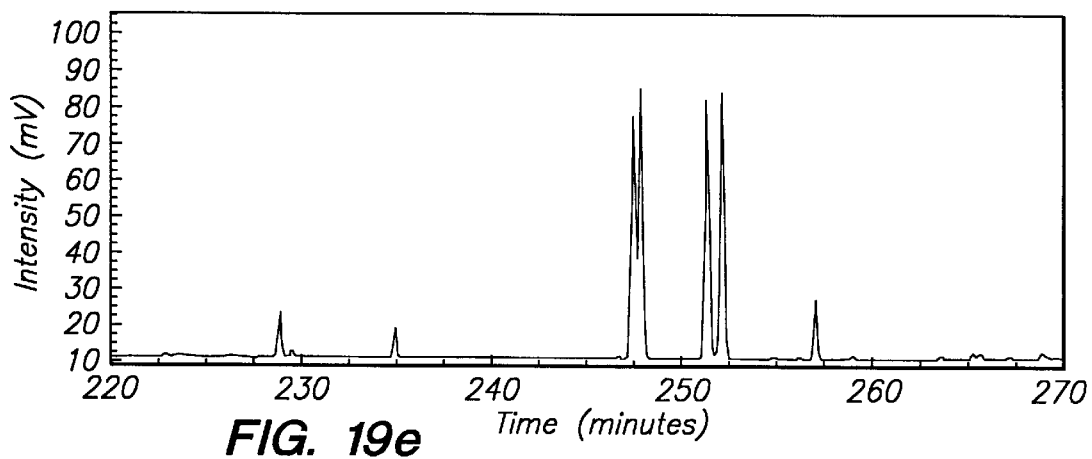

A hydrocarbon feed of 5:1 (wt:wt) o-xylene: DMN mixture (approximately 2,7-DMN:1,7-DMN:1,6-DMN:1,5-DMN=2:2:2:1 by weight) was hydroisomerized in a reactor with PdSN catalyst at 420° F., 500 psig, 1.0 ml/hr feed, 40 ml/min $H_2$ and 0.5 g catalyst. The hydroisomerization products including the solvent o-xylene were collected and then dehydrogenated by being fed to PtS/Na-ZSM-5 in a reactor at 850° F., 100 psig, 1.0 ml/hr feed, 23 ml/min $H_2$ and 0.5 g catalyst. The DMN mixture feed used for hydroisomerization is shown in FIG. 19a. The feed for the dehydrogenation (which is the hydroisomerization products of DMN mixture) is shown in chromatographic form in FIG. 19b. The result of the dehydrogenation is shown in chromatographic form in FIG. 19c. The results (significant peaks of 2,7-, 2,6-, 1,7- and 1,6-DMN and lesser peak of 1,5-DMN) are shown on an expanded scale in FIG. 19e in comparison to DMN mixture (used as feed for hydroisomerization) in FIG. 19d. The detailed GC peak identification is demonstrated in FIGS. 1a, 1b, 2a, 2b, 3a, 3b, 4a, 4b, 5a, 5b, 10a and 10b. The compositions of the DMN mixture feed (for the hydroisomerization), the dehydrogenation feed (hydroisomerization products of DMN mixture), and the dehydrogenation product are shown in weight % in Table XXV.

TABLE XXV

|  | DMN mixture (used as feed for hydro-isomerization) | Feed for dehydrogenation (made from DMN mixture hydro-isomerization) | Product of dehydrogenation |
|---|---|---|---|
| DMN's (total) | 100 | 1.5 | 87.8 |
| 2,7-DMN | 28.3 | 0.4 | 23.2 |
| 2,6-DMN | 0 | 0.3 | 18.3 |
| 1,7-DMN | 28.7 | 0.1 | 20.4 |
| 1,6-DMN | 28.4 | 0.1 | 21.0 |
| 1,5-DMN | 14.6 | 0.1 | 4.0 |
| Other DMN's | 0 | 0.5 | 0.9 |
| DMD's + other C12's | 0 | 45.1 | 6.3 |
| DMT's (total) | 0 | 53.4 | 2.1 |
| 1,5-DMT | 0 | 2.2 | 0.1 |
| 1,6-DMT | 0 | 6.8 | 0.1 |
| 2,5-DMT | 0 | 5.5 | 0.1 |
| 1,7-DMT | 0 | 6.6 | 0.2 |
| 2,8-DMT | 0 | 5.1 | 0.1 |
| 2,7-DMT | 0 | 12.1 | 0.2 |
| 2,6-DMT | 0 | 12.1 | 0.3 |
| 1,4-DMT | 0 | 0 | 0 |
| Other DMT's | 0 | 3.0 | 1.0 |
| 1-MN | 0 | 0 | 1.3 |
| 2-MN | 0 | 0 | 1.9 |
| TMN's | 0 | 0 | 0.6 |

Although a few embodiments of the invention have been described in detail above, it will be appreciated by those skilled in the art that various modifications and alterations can be made to the particular embodiments shown without materially departing from the novel teachings and advantages of the invention. Accordingly, it is to be understood that all such modifications and alterations are included within the spirit and scope of the invention as defined by the following claims.

What is claimed is:

1. A method of making 2,6-dimethylnaphthalene comprising:
   (a) contacting a hydrocarbon feed comprising a dimethylnaphthalene isomer or mixture of isomers selected from the group consisting of 1,6-dimethylnaphthalene, 1,5-dimethylnaphthalene, 2,7-dimethylnaphthalene, 1,7-dimethylnaphthalene, 1,8-dimethylnaphthalene, and partially or fully hydrogenated counterparts thereof with a catalyst, the catalyst being a combination of an acidic catalyst with a metal, in the presence of hydrogen gas to obtain a hydroisomerized mixture comprising 2,6-dimethyltetralin, 2,6-dimethyldecalin; and
   (b) contacting the hydroisomerized mixture with a reforming catalyst to dehydrogenate the hydroisomerized mixture thus obtaining a dehydrogenated mixture comprising 2,6-dimethylnaphthalene.

2. The method of claim 1 further comprising recycling through step (a) and step (b) hydrocarbons other than 2,6-dimethylnaphthalene, 2,6-dimethyldecalin, and 2,6-dimethyltetralin from the hydroisomerized mixture produced in step (a) and/or hydrocarbons other than 2,6-dimethylnaphthalene from the dehydrogenated mixture of step (b) to yield additional 2,6-DMN.

3. The method of claim 1 further comprising contacting the feed mixture before and/or after step (a) with an acidic catalyst under conditions sufficient to maximize production of 2,6-DMN through intra-triad isomerization of DMN.

4. The method of claim 1 wherein the feed mixture is neat or in solution.

5. The method of claim 1 wherein the weight hourly space velocity is in a range from 0.1 to 100 $hr^{-1}$.

6. The method of claim 1 wherein the molar ratio of hydrogen to hydrocarbon in step (a) is in a range from 0.1 to 100.

7. The method of claim 1 wherein step (a) is conducted at a temperature in a range from 300° F. to 1000° F.

8. The method of claim 1 wherein the acidic catalyst in step (a) is selected from the group consisting of oxides of silica, boron, aluminum, gallium, germanium, iron, chromium, zirconium and mixtures thereof.

9. The method of claim 1 wherein the metal in step (a) is selected from the group consisting of nickel, copper and a noble metal.

10. The method of claim 9 wherein the metal is in a range from 0.1 to 10% by weight of the catalyst in step (a).

11. The method of claim 9 wherein the metal is selected from the group consisting of palladium and platinum.

12. The method of claim 8 wherein the acidic catalyst in step (a) is selected from the group consisting of amorphous materials and zeolitic materials.

13. The method of claim 12 wherein the acidic catalyst in step (a) is selected from the group consisting of SAPO-11, Al/B/beta catalyst, Y zeolite and amorphous silica-aluminum catalyst.

14. The method of claim 1 wherein the catalyst in step (b) comprises a catalyst which is substantially non-acidic.

15. The method of claim 14 wherein the non-acidic catalyst in step (b) is selected from the group consisting of Pt/Na-ZSM-5 and Pt/Cs/B-SSZ-42.

16. The method of claim 14 wherein the non-acidic catalyst in step (b) is sulfided.

17. The method of claim 1 wherein the catalyst in step (b) comprises an acidic reforming catalyst.

18. The method of claim 17 wherein the acidic reforming catalyst in step (b) is Pt/Re on alumina.

* * * * *